United States Patent
Lemke et al.

(10) Patent No.: US 9,085,514 B2
(45) Date of Patent: Jul. 21, 2015

(54) UNNATURAL AMINO ACIDS COMPRISING A CYCLOOCTYNYL OR TRANS-CYCLOOCTENYL ANALOG GROUP AND USES THEREOF

(75) Inventors: Edward Lemke, Mannheim (DE); Carsten Schultz, Heidelberg (DE); Tilman Plass, Heidelberg (DE); Sigrid Milles, Mannheim (DE); Christine Koehler, Forst (DE)

(73) Assignee: EMBL, Heidelberg (DE)

( * ) Notice: Subject to any disclaimer, the term of this patent is extended or adjusted under 35 U.S.C. 154(b) by 54 days.

(21) Appl. No.: 13/982,446

(22) PCT Filed: Feb. 3, 2012

(86) PCT No.: PCT/EP2012/051885
§ 371 (c)(1),
(2), (4) Date: Nov. 14, 2013

(87) PCT Pub. No.: WO2012/104422
PCT Pub. Date: Aug. 9, 2012

(65) Prior Publication Data
US 2014/0073764 A1 Mar. 13, 2014

Related U.S. Application Data

(60) Provisional application No. 61/462,477, filed on Feb. 3, 2011, provisional application No. 61/453,358, filed on Mar. 16, 2011.

(51) Int. Cl.
| | | |
|---|---|---|
| *A61K 38/00* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *C07C 271/22* | (2006.01) | |
| *C07C 271/34* | (2006.01) | |
| *C12P 21/02* | (2006.01) | |
| *C07K 1/13* | (2006.01) | |
| *C07K 2/00* | (2006.01) | |
| *C12P 21/00* | (2006.01) | |

(52) U.S. Cl.
CPC ............ *C07C 271/22* (2013.01); *C07C 271/34* (2013.01); *C07K 1/13* (2013.01); *C07K 2/00* (2013.01); *C12P 21/00* (2013.01); *C12P 21/02* (2013.01); *C07B 2200/09* (2013.01); *C07C 2101/18* (2013.01); *C07C 2102/24* (2013.01); *C07C 2102/42* (2013.01)

(58) Field of Classification Search
None
See application file for complete search history.

(56) References Cited

FOREIGN PATENT DOCUMENTS

| WO | WO 2007/039858 A2 | 4/2007 |
|---|---|---|
| WO | WO 2010/119389 A2 | 10/2010 |

OTHER PUBLICATIONS

Agard et al., "A Strain-Promoted [3+2] Azide—Alkyne Cycloaddition for Covalent Modification of Biomolecules in Living Systems", *J. Am Chem Soc*, 126, 15046-15047 (2004).
Chang et al., "Copper-free click chemistry in living animals", *PNAS*, vol. 107 (5), 1821-1826 (2010).
Chin et al., "Addition of p-Azido-L-phenylalanine to the Genetic Code of *Escherichia coli*", *J. Am. Chem. Soc.*, 124, 9026-9027 (2002).
Chin et al., "An Expanded Eukaryotic Genetic Code", *Science*, vol. 301, 964-967 (2003).
Deforest et al., "Sequential click reactions for synthesizing and patterning three-dimensional cell microenvironments", *Nature Materials*, vol. 8, 659-664 (2009).
Devaraj et al., "Tetrazine-Based Cycloadditions: Application to Pretargeted Live Cell Imaging", *Bioconjug Chem.*, 19(12), 2297-2299 (2008).
Devaraj et al., "Fast and Sensitive Pretargeted Labeling of Cancer Cells via Tetrazine/Trans-Cyclooctene Cycloaddition", *Angew Chem Int Ed Engl*, 48(38), 7013-7016 (2009).
Devaraj et al., "Bioorthogonal Turn-On Probes for Imaging Small Molecules inside Living Cells", *Angew Chem Int Ed*, 49, 2869-2872 (2010).
Dommerholt et al., "Readily Accessible Bicyclononynes for Bioorthogonal Labeling and Three-Dimensional Imaging of Living Cells", *Angew Chem Int Ed*, 49, 9422-9425 (2010).
Kolb et al., "Click Chemistry: Diverse Chemical Function from a Few Good Reactions", *Angew Chem Int Ed 40*, 2004-2021 (2001).
Liu et al., "Adding New Chemistries to the Genetic Code", *Ann Rev Biochem*, 79(1), 413-444 (2010).
Neef et al., "Selective Fluorescence Labeling of Lipids in Living Cells", *Angew Chem Int Ed*, 48, 1498-1500 (2009).

(Continued)

*Primary Examiner* — Marcela M Cordero Garcia
*Assistant Examiner* — Kaipeen Yang
(74) *Attorney, Agent, or Firm* — Viksnins Harris & Padys PLLP

(57) ABSTRACT

The present invention relates to unnatural amino acids comprising a cyclooctynyl or trans-cyclooctenyl analog group and having formula (I) or an acid or base addition salt thereof. The invention also relates to the use of said unnatural amino acids, kits and processes for preparation of polypeptides that comprise one or more than one cyclooctynyl or trans-cyclooctenyl analog group. These polypeptides can be covalently modified by in vitro or in vivo reaction with compounds comprising an azide, nitrile oxide, nitrone, diazocarbonyl or 1,2,4,5-tetrazine group.

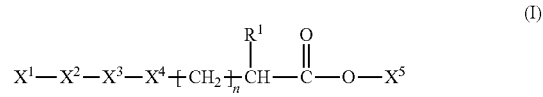

29 Claims, 6 Drawing Sheets

(56) References Cited

OTHER PUBLICATIONS

Nguyen et al., "Genetic Encoding and Labeling of Aliphatic Azides and Alkynes in Recombinant Proteins via a Pyrrolysyl-tRNA Synthetase/tRNACUA Pair and Click Chemistry", *J Am Chem Soc*, 131, 8720-8721 (2009).

Palomo et al., "Diels—Alder Cycloaddition in Protein Chemistry", *Eur J Org Chem*, 33, 6303-6314 (2010).

Patent Cooperation Treaty, International Searching Authority, Search Report and Written Opinion for PCT/EP2012/051885, 11 pages, May 15, 2012.

Sanders et al., "Metal-Free Sequentials [3+2]-Dipolar Cycloadditions using Cyclooctynes and 1,3-Dipoles of Different Reactivity", *J. Am. Chem. Soc.*, 133, 949-957 (2011).

Summerer et al., "A genetically encoded fluorescent amino acid", *PNAS*, vol. 103(26), 9785-9789 (2006).

Tiefenbrunn et al., "Invited Review. Chemoselective Ligation Techniques: Modern Applications of Time-Honored Chemistry", *Biopolymers*, 94(1), 95-106 (2010).

Yanagisawa et al., "Multistep Engineering of Pyrrolysyl-tRNA Synthetase to Genetically Encode NE-(9-Azidobenzyloxycarbonyl) lysine for Site-Specific Protein Modification", *Chemistry & Biology*, 15, 1187-1197 (2008).

Figure 7
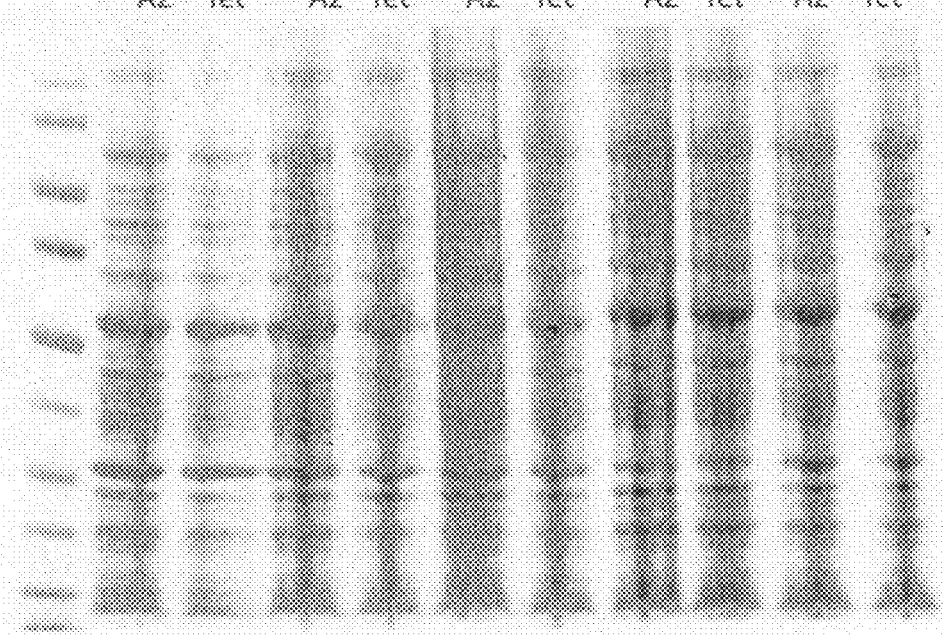

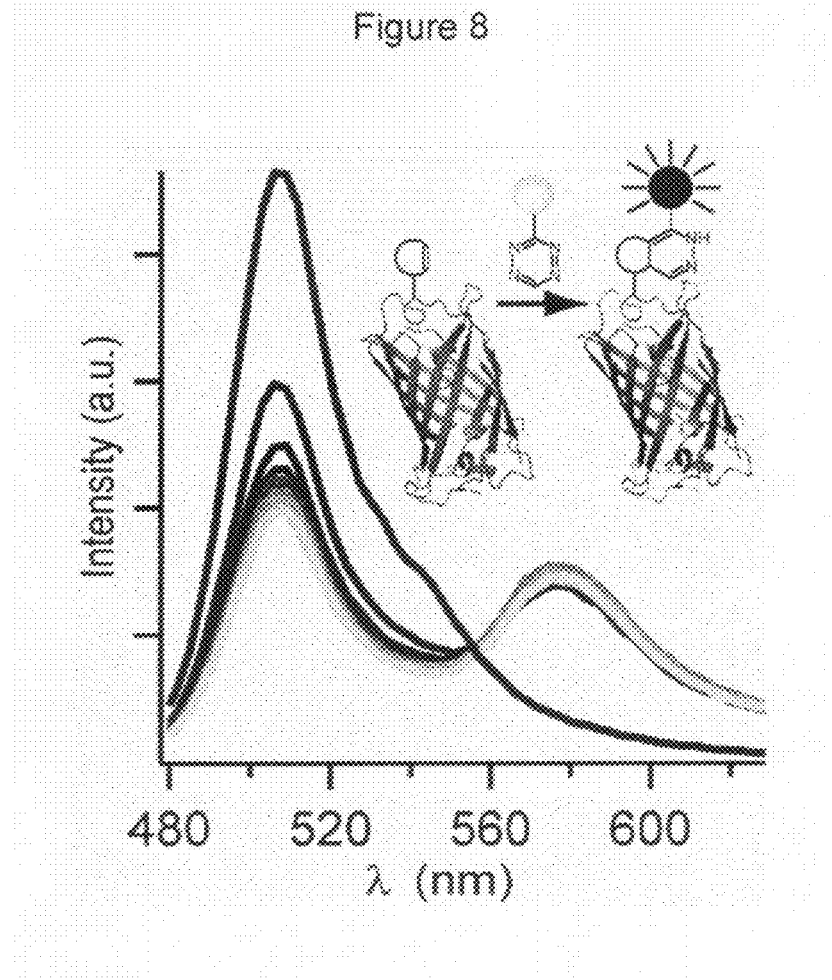

SEQUENCE LISTING

```
<160> NUMBER OF SEQ ID NOS: 2

<210> SEQ ID NO 1
<211> LENGTH: 454
<212> TYPE: PRT
<213> ORGANISM: M. maize

<400> SEQUENCE: 1

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
                20                  25                  30

Arg Ser Lys Ile Tyr Ile Glu Met Ala Cys Gly Asp His Leu Val Val
            35                  40                  45

Asn Asn Ser Arg Ser Ser Arg Thr Ala Arg Ala Leu Arg His His Lys
        50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220
```

```
Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
            245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
            275                 280                 285

Phe Arg Val Asp Lys Asn Phe Cys Leu Arg Pro Met Leu Ala Pro Asn
            290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
            325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
            355                 360                 365

His Leu Gly Ile Asp Phe Lys Ile Val Gly Asp Ser Cys Met Val Tyr
370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
            405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Glu Ser Tyr Tyr Asn
            435                 440                 445

Gly Ile Ser Thr Asn Leu
            450

<210> SEQ ID NO 2
<211> LENGTH: 454
<212> TYPE: PRT
<213> ORGANISM: Artificial Sequence
<220> FEATURE:
<223> OTHER INFORMATION: mutant M. maize pyrrolysyl tRNA synthetase

<400> SEQUENCE: 2

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
            35                  40                  45

Asn Asn Ser Arg Ser Ser Arg Thr Ala Arg Ala Leu Arg His His Lys
        50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
            85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
            115                 120                 125
```

```
Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
                180                 185                 190

Ser Gln Thr Asp Arg Leu Glu Val Leu Leu Asn Pro Lys Asp Glu Ile
            195                 200                 205

Ser Leu Asn Ser Gly Lys Pro Phe Arg Glu Leu Glu Ser Glu Leu Leu
        210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ala Pro Asn
    290                 295                 300

Leu Ala Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Phe
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Glu Ser Tyr Tyr Asn
        435                 440                 445

Gly Ile Ser Thr Asn Leu
        450
```

UNNATURAL AMINO ACIDS COMPRISING A CYCLOOCTYNYL OR TRANS-CYCLOOCTENYL ANALOG GROUP AND USES THEREOF

FIELD OF THE INVENTION

The invention relates to unnatural amino acids (UAA) comprising a cyclooctynyl or trans-cyclooctenyl analog group, and their use, kits and processes for preparation of polypeptides that comprise one or more than one cyclooctynyl or trans-cyclooctenyl analog group. These polypeptides can be covalently modified by in vitro or in vivo reaction with compounds comprising an azide, nitrile oxide, nitrone, diazocarbonyl or 1,2,4,5-tetrazine group.

BACKGROUND OF THE INVENTION

The ability to visualize biomolecules within living specimen by engineered fluorescence tags has become a major tool in modern biotechnology, cell biology, and life science. Encoding fusion proteins with comparatively large autofluorescent proteins is currently the most widely applied technique. As synthetic dyes typically offer better photophysical properties than autofluorescent proteins, alternative strategies have been developed based on genetically encoding unique tags such as Halo- and SNAP-tags, which offer high specificity but are still fairly large in size. Small tags like multi-histidine or multi-cysteine motifs may be used to recognize smaller fluorophores, but within the cellular environment they frequently suffer from specificity issues as their basic recognition element is built from native amino adds side chains. Such drawbacks may be overcome by utilizing bioorthogonal chemistry that relies on attaching unnatural moieties under mild physiological conditions.

Powerful chemistry that proceeds efficiently under physiological temperatures and in richly functionalized biological environments is the copper(I) catalyzed Huisgen type (3+2) cycloaddition between linear azides and alkynes, or the inverse electron-demand Diels-Alder (4+2) cycloaddition reaction between a strained dienophile such as trans-cyclooctene or norbornene and a 1,2,4,5-tetrazine, both forms of click chemistry (Kolb et al., Angew Chem Int Ed Engl 2001, 40:2004; Devaraj at al., Angew Chem Int Ed Engl 2009, 48:7013). However, the more established (3+2) cycloaddition requires a copper catalyst that is toxic or bacteria and mammalian cells, which strongly reduces biocompatibility of this type of click chemistry. This limitation has been overcome by Bertozzi and co-workers, who showed that the click reaction readily proceeds without the need for a cell-toxic catalyst when utilizing ring-strained alkynes as a substrate (Agard et al., J Am Chem Soc 2004, 126:15046). Copper-free click chemistry has found increasing applications in labeling biomolecules. Fluorescent dyes comprising cyclooctynyl groups were used to label carbohydrates and proteins comprising enzymatically attached azide moieties in vivo (Chang et al., Proc Natl Acad Sci USA 2010, 107:1821) and the labeling of alkyne-/cycloalkyne-modified phosphatidic acid with azido fluorophores is described in Neef and Schultz, Angew Chem Int Ed Engl 2009, 48:1498. The alternative. Diels-Alder (4+2) cycloaddition, for labeling molecules in vivo requires the reaction of a strained dienophilic group such as a trans-cyclooctenyl group or norbornenyl group with a 1,2,4,5-tetrazine fused to a small molecule probe, e.g. a fluorophore (Devaraj et al., Bioconjugate Chem 2008, 19:2297; Devaraj et al., Angew Chem Int Ed Engl 2009, 48:7013; Devaraj et al., Angew Chem Int Ed Engl 2010, 49:2869). No catalyst is required.

The translational modification of proteins by direct genetic encoding of fluorescent unnatural amino acids using an orthogonal aminoacyl tRNA/synthetase pair offers exquisite specificity, freedom of placement within the target protein and, if any, a minimal structural change. This approach was first successfully applied by Summerer et al. (Proc Natl Acad Sci USA 2006, 103:9785), who evolved a leucyl tRNA/synthetase pair from *Escherichia coli* to genetically encode the UAA dansylalanine into *Saccharomyces cerevisiae*. In response to the amber stop codon TAG, dansylalanine was readily incorporated by the host translational machinery. This approach has meanwhile been used to genetically encode several small dyes and other moieties of interest. For instance, engineered *Methanococcus jannaschii* tyrosyl tRNA[tyr]/synthetase, *E. coli* leucyl tRNA[leu]/synthetase as well as *Methanosarcina maize* and *M. barkeri* pyrrolysine tRNA[pyl]/synthetase pairs have been used to genetically encode azide moieties in polypeptides (Chin et al., J Am Chem Soc 2002, 124:9026; Chin et al., Science 2003, 301:964; Nguyen et al, J Am Chem Soc 2009, 131:8720, Yanagisawa et al., Chem Biol 2008, 15:1187). However, due to the need to evolve new aminoacyl tRNA/synthetase pairs and potential size limitations imposed by the translational machinery, larger dyes with enhanced photophysical properties and other bulky moieties have not yet been encoded.

Despite large efforts, there is still a high demand for strategies to facilitate site-specific labeling of proteins in vitro and in vivo. Thus, it was an object of the present invention to provide amino acids or analogs thereof that can be translationally incorporated in polypeptide chains and allow labeling of the resulting polypeptide in vitro as well as in vivo.

SUMMARY OF THE INVENTION

The present invention relates to compounds of formula I

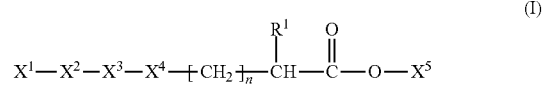

(I)

wherein:
$X^1$ has formula

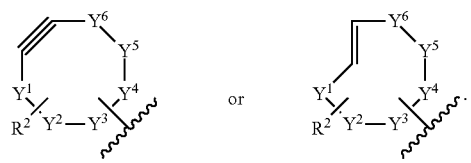

wherein:
$Y^1, Y^2, Y^3, Y^4, Y^5, Y^6$
independently are —CH$_2$—, —NH—, —S— or —O— provided that at least 4 of $Y^1, Y^2, Y^3, Y^4, Y^5, Y^6$ are —CH$_2$—;
$R^2$ is hydrogen, halogen, $C_1$-$C_4$-alkyl, CF$_3$, CN, $C_1$-$C_4$-alkoxy, —O—CF$_3$, $C_2$-$C_5$-alkanoyloxy, $C_1$-$C_4$-alkylaminocarbonyloxy or $C_1$-$C_4$-alkylthio;
$X^2$ is —CH$_2$—, —O—, —S—, —NH—, —C(O)—, —OC(O)—, —C(O)O—, —NH—C(O)— or —C(O)—NH—, or $X^2$ is >CH— or >N— wherein the carbon or the nitrogen atom together with two adjacent ring atoms of $X^1$ forms a 3-membered ring, or $X^2$ is —CH$_2$—CH<, —NH—CH< or —CH$_2$—N< wherein the two carbon atoms or the carbon and the nitrogen atom together with two adjacent ring atoms of $X^1$ form a 4-membered ring, or $X^2$ is —CH$_2$—CH$_2$—CH<, —NH—CH$_2$—CH<, —CH$_2$—NH—CH<, —CH$_2$—CH$_2$—N<,

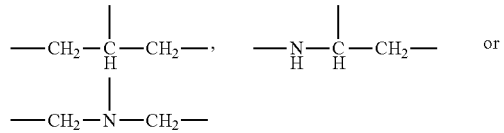

wherein the three carbon atoms or the two carbon atoms and the nitrogen atom together with two adjacent ring atoms of $X^1$ form a 5-membered ring;

$X^3$ is $C_1$-$C_6$-alkylene, —(CH$_2$—CH$_2$—O)$_m$—, —(CH$_2$—O)$_p$— or a single bond;

$X^4$ is —NH—, —C(O)—NH—, —NH—C(O)—, —NH—CH(NH$_2$)—, —CH(NH$_2$)—NH—, —NH—C(NH)—NH—, —C(O)—NH—CH(NH$_2$)—, —C(O)—NH—C(NH)—NH—, NH—CH(NH$_2$)—C(O)— or —NH—C(NH)—NH—C(O)—;

$X^5$ is hydrogen, $C_1$-$C_6$-alkyl, $C_1$-$C_6$-alkoxy-$C_1$-$C_2$-alkyl, $C_2$-$C_7$-alkanoyloxy-$C_1$-$C_2$-alkyl or $C_2$-$C_7$-alkanoylsulfanyl-$C_1$-$C_2$-alkyl;

$R^1$ is —OH or —NH$_2$;

n is an integer from 1 to 4;

m is an integer from 1 to 6; and p is an integer from 1 to 6, or an acid or base addition salt thereof.

The compounds or salts of the invention can be translationally incorporated in a polypeptide that is encoded by a polynucleotide comprising one or more than one selector codon(s).

The present invention thus also relates to a process for preparing a target polypeptide having one or more than one cyclooctynyl or trans-cyclooctenyl analog group, the process comprising:

a) providing a translation system comprising:
   (i) an aminoacyl tRNA synthetase, or a polynucleotide encoding it;
   (ii) a compound or salt of the invention;
   (iii) a tRNA having an anticodon to a selector codon, or a polynucleotide encoding said tRNA; and
   (iv) a polynucleotide encoding the target polypeptide and comprising one or more than one selector codon(s),
   wherein the aminoacyl tRNA synthetase (i) is capable of specifically acylating the tRNA (iii) with the compound or salt (ii);
b) allowing translation of the polynucleotide (iv) thereby incorporating the compound (II) into the target polypeptide at the position(s) encoded by the selector codon(s); and
c) optionally recovering the resulting polypeptide.

The present invention thus also relates to a polypeptide comprising one or more than one residue of formula II

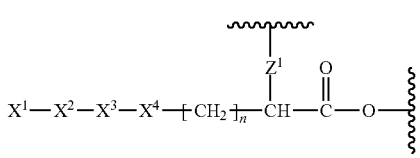

wherein:

$X^1$ has formula

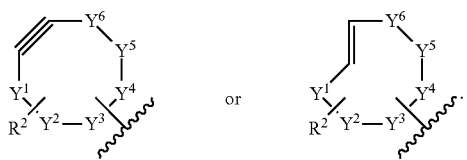

wherein:

$Y^1, Y^2, Y^3, Y^4, Y^5, Y^6$ independently are —CH$_2$—, —NH—, —S— or —O— provided that at least 4 of $Y^2, Y^3, Y^4, Y^5, Y^6$ are —CH$_2$—;

$R^2$ is hydrogen, halogen, $C_1$-$C_4$-alkyl, CF$_3$, CN, $C_1$-$C_4$-alkoxy, —O—CF$_3$, $C_2$-$C_5$-alkanoyloxy, $C_1$-$C_4$-alkylaminocarbonyloxy or $C_1$-$C_4$-alkylthio;

$X^2$ is —CH$_2$—, —O—, —S—, —NH—, —C(O)—, —OC(O)—, —C(O)O—, —NH—C(O)— or —C(O)—NH—, or $X^2$ is >CH— or >N— wherein the carbon or nitrogen atom together with two adjacent ring atoms of $X^1$ forms a 3-membered ring, or $X^2$ is —CH$_2$—CH<, —NH—CH< or —CH$_2$—N< wherein the two carbon atoms or the carbon and the nitrogen atom together with two adjacent ring atoms of $X^1$ form a 4-membered ring, or $X^2$ is —CH$_2$—CH$_2$—CH<, —NH—CH$_2$—CH<, —CH$_2$—NH—CH<, —CH$_2$—CH$_2$—N<,

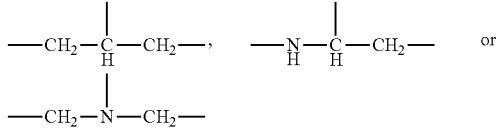

wherein the three carbon atoms or the two carbon atoms and the nitrogen atom together with two adjacent ring atoms of $X^1$ form a 5-membered ring;

$X^3$ is $C_1$-$C_6$-alkylene, —(CH$_2$—CH$_2$—O)$_m$—, —(CH$_2$—O)$_p$— or a single bond;

$X^4$ is —NH—, —C(O)—NH—, —NH—C(O)—, —NH—CH(NH$_2$)—, —CH(NH$_2$)—NH—, —NH—C(NH)—NH—, —C(O)—NH—CH(NH$_2$)—, —C(O)—NH—C(NH)—NH—, NH—CH(NH$_2$)—C(O)— or —NH—C(NH)—NH—C(O)—;

$Z^1$ is —O— or —NH—;

n is an integer from 1 to 4;

m is an integer from 1 to 6; and p is an integer from 1 to 6.

The present invention further relates to kits for preparing a polypeptide having one or more than one cyclooctynyl or trans-cyclooctenyl analog group (target polypeptide). The kits comprise a compound or salt of the invention and optionally one or more means for preparing the polypeptide, such as one or more than one polynucleotide encoding an aminoacyl tRNA synthetase, a tRNA as described herein; a polynucleotide encoding a reporter protein; and/or further means for translation of a polynucleotide encoding said target polypeptide.

Like trans-cyclooctenyl groups norbornenyl groups are known to react with 1,2,4,5-tetrazines in inverse-electron-demand Diels-Alder cycloadditions (Devaraj et al., Bioconjugate Chem 2008, 19:2297). The present invention therefore also pertains to unnatural amino acids comprising a norbornenyl group, their use, kits and processes for preparation of polypeptides that comprise one or more than one norbornenyl group, wherein what is disclosed herein with regard to trans-cyclooctenyl applies in an analogous manner to norbornenyl.

BRIEF DESCRIPTION OF THE FIGURES

FIG. 7 shows analysis of proteins produced by *E. coli* as described in example D. Cultures expressing $GFP^{TAG \to 1}$ (+1), $GFP^{TAG \to 13}$ (+13), $GFP^{TAG \to 16}$ (+16), $GFP^{TAG \to 17}$ (+17) or $GFP^{TAG}$ with propargyllysine (negative control) were treated with TAMRA-azide (Az), or TAMRA-tetrazine (Tet) and subjected to SDS-PAGE. After electrophoresis a fluorescent image of the gel (a) was taken. The proteins separated in the SDS polyacrylamide gel were visualized by Coomassie staining (b).

FIG. 8 illustrates increasing FRET from GFP to TAMRA observed with *E. coli* expressed $GFP^{TAG \to 13}$ during labeling with TAMRA-tetrazine. Fluorescence spectra (excitation at 450 nm, emission 470-650 nm) were recorded over time (from dark- to light-colored graph).

DETAILED DESCRIPTION OF THE INVENTION

Figure 1:
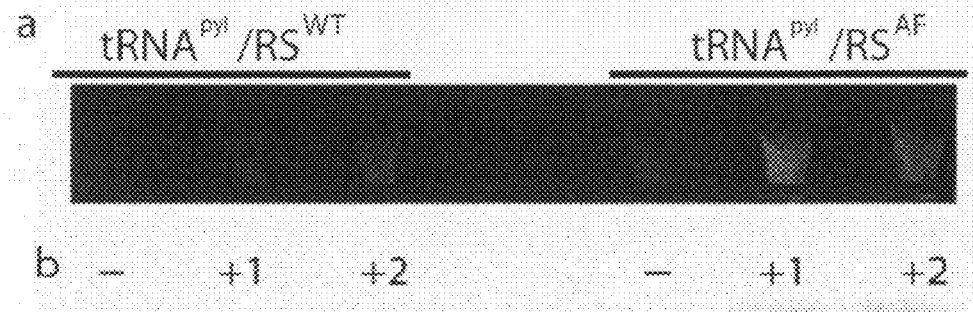
FIG. 1 shows fluorescent images of *E. coli* cultures expressing $GFP^{TAG}$ (a), and $GFP^{TAG}$ bands in a Coomassie stained gel from an SDS-PAGE of His-tagged protein, purified from *E. coli* protein expression cultures (b). $GFP^{TAG}$ was expressed in the presence of wildtype ($tRNA^{pyl}/RS^{WT}$) or mutant ($tRNA^{pyl}/RS^{AF}$) pyrrolysyl tRNA/pyrrolysyl tRNA synthetase pairs in media supplemented with either NaOH ("−"), compound 1 ("+1"), or compound 2 ("+2"). Sizes of marker proteins are given in kDa.
Figure 2:
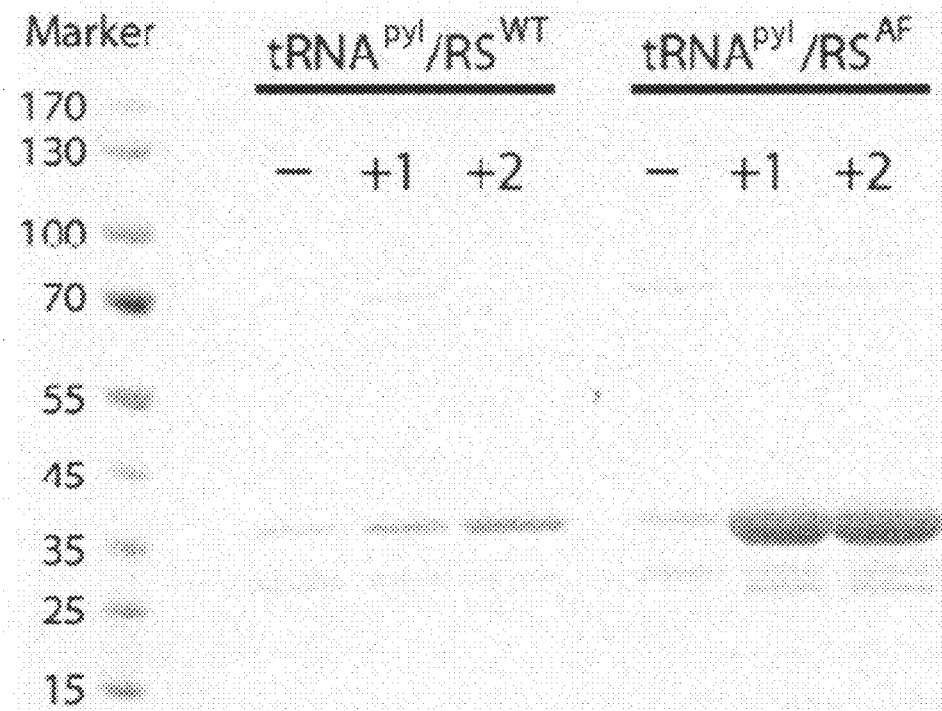
FIG. 2 shows the Coomassie stained gel of FIG. 1b in full size.

The compounds and salts of the invention are unnatural amino acids that can be translationally incorporated in polypeptide chains.

The term "unnatural amino acid" refers to an amino acid that is not one of the 20 canonical amino acids or selenocysteine. The term also refers to amino acid analogs, e.g. wherein the α-amino group is replaced by a hydroxyl group.

The compounds or salts of the invention possess centers of asymmetry and may exist in different spatial arrangements or as different tautomers. For preparation of polypeptides with cyclooctynyl or trans-cyclooctenyl analog groups, enantiomeric mixtures, in particular racemates, diastereomeric mixtures and tautomeric mixtures may be used. Alternatively, the respective essentially pure enantiomers, diastereomers and tautomers of the compounds or salts of the invention may be used for such purpose.

The organic moieties mentioned in the above definitions of the variables are like the term alkyl collective terms for individual listings of the individual group members. The prefix $C_{n-m}$ indicates in each case the possible number of carbon atoms in the group.

The term halogen denotes in each case a fluorine, bromine, chlorine or iodine radical, in particular a fluorine radical.

$C_1$-$C_6$-Alkyl is a straight-chain or branched alkyl group having from 1 to 6, in particular 1 to 4 or 1 to 3 carbon atoms. Examples include methyl, $C_2$-$C_4$-alkyl such as ethyl, n-propyl, iso-propyl, n-butyl, 2-butyl, iso-butyl or tert-butyl, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

$C_1$-$C_4$-Alkylene is straight-chain or branched alkylene group having from 1 to 4 carbon atoms. Examples include methylene and 1,2-ethylene. A further example is 1,3-propylene.

$C_1$-$C_6$-Alkylene is straight-chain or branched alkylene group having from 1 to 6 carbon atoms. Examples include methylene, ethylene, 1,2-ethylene, 1,3-propylene, isopropylene, 1-4-butylene and 1-5-pentylene.

$C_1$-$C_6$-Alkoxy is a radical of the formula R—O—, wherein R is a straight-chain or branched alkyl group having from 1 to 6, in particular 1 to 4 or 1 to 3 carbon atoms as defined herein.

$C_2$-$C_7$-Alkanoyloxy is a radical of the formula R—(CO)—O—, wherein R is a straight-chain or branched alkyl group having from 1 to 6, in particular 1 to 4 or 1 to 3 carbon atoms as defined herein.

$C_1$-$C_6$-Alkylaminocarbonyloxy is a radical of the formula R—NH—(CO)—O—, wherein R is a straight-chain or branched alkyl group having from 1 to 6, in particular 1 to 4 or 1 to 3 carbon atoms as defined herein.

$C_1$-$C_4$-Alkylthio is a radical of the formula R—S—, wherein R is an alkyl radical having from 1 to 4, preferably from 1 to 3 carbon atoms as defined herein.

$C_2$-$C_7$-Alkanoylsulfanyl is a radical of the formula R—(CO)—S—, wherein R is a straight-chain or branched alkyl group having from 1 to 6, in particular 1 to 4 or 1 to 3 carbon atoms as defined herein.

The term cyclooctynyl analog group denotes an unsaturated cycloaliphatic radical having 8 carbon atoms and one triple bond in the ring structure, wherein 1 or 2 carbon atoms may be replaced by an oxygen, sulfur and/or nitrogen atom. In particular, the term cyclooctynyl analog group denotes a moiety of formula:

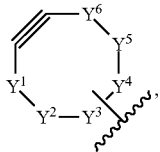

wherein $Y^1$, $Y^2$, $Y^3$, $Y^4$, $Y^5$, $Y^6$ independently are —$CH_2$—, —NH—, —S— or —O—, provided that at least 4 of $Y^1$, $Y^2$, $Y^3$, $Y^5$, $Y^6$, $Y^6$ are —$CH_2$—.

The term cyclooctynyl group denotes a cyclooctynyl analog group as defined above, wherein all of $Y^1$, $Y^2$, $Y^3$, $Y^4$, $Y^5$, $Y^6$ are —$CH_2$—. In particular, the term cyclooctynyl denotes a moiety of formula:

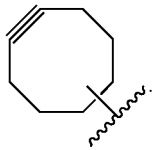

The term trans-cyclooctenyl analog group denotes an unsaturated cycloaliphatic radical having 8 carbon atoms and one double bond that is in trans configuration in the ring structure, wherein 1 or 2 carbon atoms may be replaced by an oxygen, sulfur and/or nitrogen atom. In particular, the term trans-cyclooctenyl analog group denotes a moiety of formula:

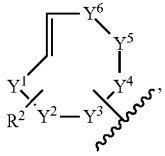

wherein $Y^1$, $Y^2$, $Y^3$, $Y^4$, $Y^5$; $Y^6$ independently are —$CH_2$—, —NH—, —S— or —O—, provided that at least 4 of $Y^1$, $Y^2$, $Y^3$, $Y^4$, $Y^5$, $Y^6$ are —$CH_2$—.

The term trans-cyclooctenyl denotes a trans-cyclooctenyl analog group as defined above, wherein all of $Y^1$, $Y^2$, $Y^3$, $Y^4$, $Y^5$, $Y^6$ are —$CH_2$—. In particular, the term trans-cyclooctenyl denotes a moiety of formula:

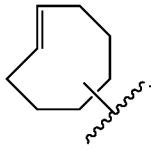

Unless indicated otherwise, the term "substituted" means that a radical is substituted with 1, 2 or 3, especially 1 or 2, substituent(s) which are in particular selected from the group consisting of halogen, $C_1$-$C_4$-alkyl, CN, $CF_3$, —O—$CF_3$, $C_1$-$C_4$-alkoxy, $C_2$-$C_4$-alkanoyloxy, $C_1$-$C_4$-alkylaminocarbonyloxy and $C_1$-$C_4$-alkylthio.

With respect to the compounds capability of being translationally incorporated in a polypeptide chain, the variables $X^1$, $X^2$, $X^3$, $X^4$, $X^5$, $Y^1$, $Y^2$, $Y^3$, $Y^4$, $Y^5$, $Y^6$, n, m, p, $R^1$ and $R^2$ preferably have the following meanings which, when taken alone or in combination, represent particular embodiments of the unnatural amino acids of the formula I or any other formula, disclosed herein.

$X^1$ has formula:

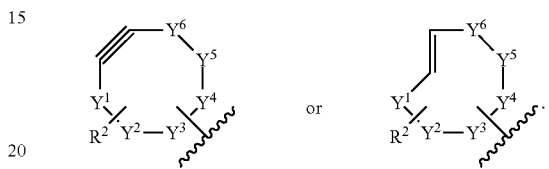

wherein $Y^1$, $Y^2$, $Y^3$, $Y^4$, $Y^5$, $Y^6$ independently are —$CH_2$—, —NH—, —S— or —O—, provided that at least 4 of $Y^1$, $Y^2$, $Y^3$, $Y^4$, $Y^5$, $Y^6$ are —$CH_2$—; and wherein $R^2$ is as defined herein.

According to one embodiment, $X^1$ is a cyclooctynyl analog group of formula

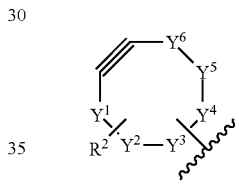

wherein $Y^1$, $Y^2$, $Y^3$, $Y^4$, $Y^5$, $Y^6$ and $R^2$ are as defined herein.

According to another embodiment, $X^1$ is a trans-cyclooctenyl analog group of formula

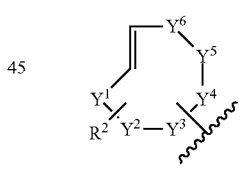

wherein $Y^1$, $Y^2$, $Y^3$, $Y^4$, $Y^5$, $Y^6$ and $R^2$ are as defined herein.

The cyclooctynyl or trans-cyclooctenyl analog $X^1$ group may be attached to $X^2$ by a ring atom in α-, β- or γ-position relative to the triple or double bond. In case. $X^2$ together with two adjacent ring atoms of $X^1$ forms a 3-, 4- or 5-membered ring, the $X^1$ group may be attached to $X^2$ via $Y^1$ and $Y^2$, $Y^2$ and $Y^3$, $Y^3$ and $Y^4$, $Y^4$ and $Y^5$, or $Y^5$ and $Y^6$. It will readily be appreciated that $X^2$ is C- or N-bound to one or two of $Y^1$, $Y^2$, $Y^3$, $Y^4$, $Y^5$, $Y^6$ in $X^1$ (whereby —$CH_2$— or —NH— become >CH— or >N—, respectively).

According to a particular embodiment, the cyclooctynyl or trans-cyclooctenyl analog group is attached to $X^2$ by the ring atom in α-position relative to the triple or double bond, i.e. via $Y^1$ or $Y^6$. In case $X^2$ together with two adjacent ring atoms of $X^1$ forms a 3-, 4- or 5-membered ring, it is a particular embodiment if the cyclooctynyl or trans-cyclooctenyl analog group is attached to $X^2$ via $Y^3$ and $Y^4$.

The cyclooctynyl or trans-cyclooctenyl analog group may be unsubstituted R² is hydrogen) or substituted with one or more than one radical R². Thus, there may be one or more than one substituent R². More particularly, there may be up to 5 substituents R². Preferably there are 1, 2 or 3 substituents R². Formula (I) may thus be depicted as follows:

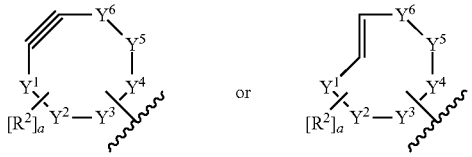

wherein a is zero, 1, 2, 3, 4 or 5.

If there is more than one radical R², these may be the same or different radicals and two radicals R² may be bound to the same or different atoms. For example, R² may be two fluorine atoms bound to one carbon ring atom.

R² is hydrogen, halogen, C₁-C₄-alkyl, CF₃, CN, C₁-C₄-alkoxy, —O—CF₃, C₂-C₅-alkanoyloxy, C₁-C₄-alkylaminocarbonyloxy or C₁-C₄-alkylthio.

According to a particular embodiment, R² is halogen, preferably fluorine.

According to a further particular embodiment, X¹ is a cyclooctynyl analog group, and R² is halogen, preferably fluorine.

When X¹ is a cyclooctynyl analog group and R² is halogen, e.g. fluorine, is particularly preferred that R² is attached at the ring atom which is adjacent to the triple bond.

According to a further particular embodiment, R² is C₂-C₅-alkanoyloxy or C₁-C₄-alkylaminocarbonyloxy.

According to a particular embodiment, X¹ is cyclooctynyl (all of Y¹, Y², Y³, Y⁴, Y⁵, Y⁶ are —CH₂—), i.e. X¹ has the formula

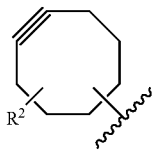

wherein R² is as defined herein.

These substituted or unsubstituted cyclooctynyl groups may be attached to X² by a ring atom in α-, β- or γ-position relative to the triple bond. According to a particular embodiment, X¹ has a formula

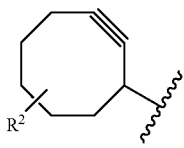

wherein R² is as defined herein.

According to another particular embodiment, X¹ is azacyclooctynyl, i.e. X¹ has the formula

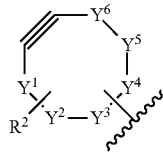

wherein one of Y¹, Y², Y³, Y⁴, Y⁵, Y⁶ is —NH— while the remaining five of Y¹, Y², Y³, Y⁴, Y⁵, Y⁶ are —CH₂—), and R² is as defined herein. Particular azacyclooctynyl residues include 1-azacyclooctyn-1-yl radicals which are bound to X² via the nitrogen atom, e.g. wherein X¹ has a formula selected from

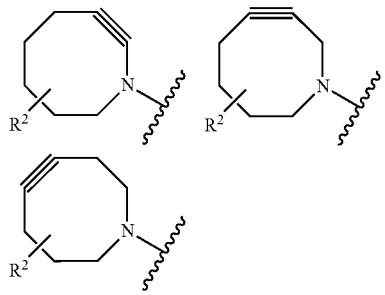

wherein R² is as defined herein.

According to one particular embodiment, X¹ is unsubstituted cyclooctynyl.

According to another particular embodiment, X¹ is cyclooctynyl substituted with one or two halogen atoms. e.g. fluorine atoms, attached at the ring atom which is adjacent to the triple bond.

According to another particular embodiment, X¹ is a trans-cyclooctenyl, i.e. X¹ has the formula

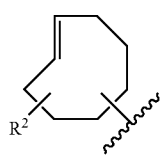

wherein R² is as defined herein.

These substituted or unsubstituted trans-cyclooctenyl groups may be attached to X² by a ring atom in α-, β- or γ-position relative to the double bond. According to a particular embodiment, X¹ has the formula

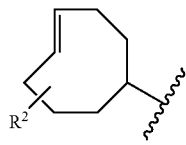

wherein R² is as defined herein.

X² is —CH₂—, —O—, —S—, —NH—, —C(O)—, —OC(O)—, —C(O)O—, —NHC(O)— or —C(O)NH—.

Preferably, X² is —O—.

Alternatively, X² is >CH— or >N— wherein the carbon or the nitrogen atom together with two adjacent ring atoms of X¹ forms a 3-membered ring; or $X^2$ is —$CH_2$—CH<, —NH—CH< or —$CH_2$—N< wherein the two carbon atoms or the carbon and the nitrogen atom together with two adjacent ring atoms of $X^1$ form a 4-membered ring; or $X^2$ is —$CH_2$—$CH_2$—CH<, —NH—$CH_2$—CH<, —$CH_2$—NH—CH<, —$CH_2$—$CH_2$—N<,

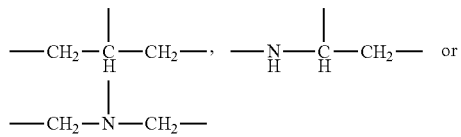

wherein the three carbon atoms or the two carbon atoms and the nitrogen atom together with two adjacent ring atoms of $X^1$ form a 5-membered ring. For example, $X^1$—$X^2$— has a formula

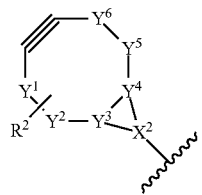

wherein $Y^1$, $Y^2$, $Y^5$, $Y^6$, $X^2$ and $R^2$ are as defined herein, and $Y^3$ and $Y^4$ are independently selected from >CH— or >N—, wherein it is preferred if both $Y^3$ and $Y^4$ are >CH—. Such bicyclo[6.1.0]nonynyl, bicyclo[6.2.0]decynyl and bicyclo[6.3.0]undecynyl analog groups are understood to comprise the substituted or unsubstituted cyclooctynyl analog group of the invention.

In case $X^2$ together with two adjacent ring atoms of $X^1$ forms a 3-, 4- or 5-membered ring, it is a particular embodiment if $X^1$—$X^2$— has a formula

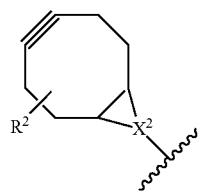

wherein $R^2$ and $X^2$ are as defined herein. Bicyclo[6.1.0]nonynyl groups (i.e. $X^2$ is >CH—) represent a particular embodiment of the invention.

According to another embodiment, $X^1$—$X^2$— has a formula

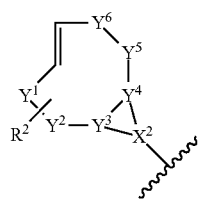

wherein $Y^1$, $Y^2$, $Y^5$, $Y^6$, $X^2$ and $R^2$ are as defined herein, and $Y^3$ and $Y^4$ are independently selected from >CH— or >N—, wherein it is preferred if both $Y^3$ and $Y^4$ are >CH—. Such bicyclo[6.1.0]-trans-nonenyl, bicyclo[6.2.0]-trans-decenyl and bicyclo[6.3.0]-trans-undecenyl analog groups are understood to comprise the substituted or unsubstituted trans-cyclooctynyl analog group of the invention.

In case $X^2$ together with two adjacent ring atoms of $X^1$ forms a 3-, 4- or 5-membered ring, it is a particular embodiment if $X^1$—$X^2$— has a formula

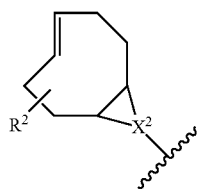

wherein $R^2$ and $X^2$ are as defined herein. Bicyclo[6.1.0]-trans-nonenyl groups (i.e. $X^2$ is >CH—) represent a particular embodiment of the invention.

$X^3$ is $C_1$-$C_6$-alkylene, —$(CH_2$—$CH_2$—O$)_m$— or a single bond; and m is 1, 2, 3, 4, 5 or 6.

In connection with $X^3$, $C_1$-$C_6$-alkylene preferably refers to straight-chain alkylene.

According to a preferred embodiment, $X^3$ is —$CH_2$—$CH_2$—O— or a single bond.

Alternatively, is —$(CH_2$—O$)_p$—; and p is 1, 2, 3, 4, 5 or 6. According to a particular embodiment, $X^3$ is —$CH_2$—O— (i.e., p is 1).

According to a particular embodiment, the structural element —$X^2$—$X^3$— comprises from 1 to 6 atoms in the main chain, such as 1, 2, 3 or 4 atoms in the main chain.

According to a particular embodiment, —$X^2$—$X^3$— is —O— or —O—$(CH_2)_2$—O—. In, case $X^2$ together with two adjacent ring atoms of $X^1$ forms a 3-, 4- or 5-membered ring, $X^3$ being —$CH_2$—O— represents a further particular embodiment.

According to a further particular embodiment, $X^1$—$X^2$—$X^3$— is $X^1$—O— or $X^1$—O—$(CH_2)_2$—O—, wherein $X^1$ is as defined herein, preferably unsubstituted cyclooctynyl or unsubstituted trans-cyclooctenyl.

According to a further particular embodiment, $X^1$—$X^2$—$X^3$— is $X^1$—$X^2$—$CH_2$—O—, wherein $X^1$ is as defined herein, preferably unsubstituted cyclooctynyl, and $X^2$ is >CH— or >N— wherein the carbon or the nitrogen atom together with two adjacent ring atoms of $X^1$ forms a 3-membered ring; or $X^2$ is —$CH_2$—CH<, —NH—CH< or —$CH_2$—N< wherein the two carbon atoms or the carbon and the nitrogen atom together with two adjacent ring atoms of $X^1$ form a 4-membered ring; or $X^2$ is —$CH_2$—$CH_2$—CH<, —NH—$CH_2$—CH<, —$CH_2$—NH—CH<, —$CH_2$—$CH_2$—N<,

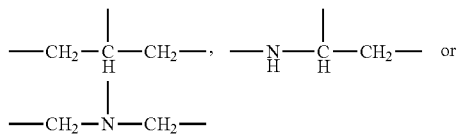

wherein the three carbon atoms or the two carbon atoms and the nitrogen atom together with two adjacent ring atoms of $X^1$ form a 5-membered ring.

$X^4$ is —NH—, —C(O)—NH—, —NH—C(O)—, —NH—CH(NH$_2$)—, —CH(NH$_2$)—NH—, —NH—C (NH)—NH—, —C(O)—NH—CH(NH$_2$)—, —C(O)—NH—C(NH)—NH—, NH—CH(NH$_2$)—C(O)— or —NH—C(NH)—NH—C(O)—.

In particular, X$^4$ is —NH—, —C(O)—NH—, —NH—CH(NH$_2$)—, —NH—C(NH)—NH—, —C(O)—NH—CH(NH$_2$)— or —C(O)—NH—C(NH)—NH—.

According to a preferred embodiment, X$^4$ is —C(O)—NH—.

n is an integer from 1 to 4.

According to a particular embodiment, n is 3 or 4.

According to a preferred embodiment, n is 4.

According to a particular embodiment, —X$^4$—(CH$_2$)$_n$— is —NH—(CH$_2$)—, —NH—C(O)—(CH$_2$)$_n$—, —NH—CH(NH$_2$)—(CH$_2$)$_n$—, —NH—C(NH)—NH—(CH$_2$)$_n$—, —C(O)—NH—CH(NH$_2$)—(CH$_2$)$_n$— or —C(O)—NH—C(NH)—NH—(CH$_2$)$_n$—, wherein n is preferably 3 or 4.

According to a preferred embodiment, —X$^4$—(CH$_2$)$_n$— is —C(O)—NH—(CH$_2$)$_n$—, wherein n is preferably 3 or 4.

According to a further particular embodiment, —X$^4$—(CH$_2$)$_n$— is —NH—(CH$_2$)$_4$—, —NH—C(O)—CH$_2$—, —NH—C(O)—(CH$_2$)$_2$—, —NH—CH(NH$_2$)—(CH$_2$)$_3$—, —NH—CH(NH$_2$)—(CH$_2$)$_4$—, —NH—C(NH)—NH—(CH$_2$)$_3$—, —C(O)—NH—CH(NH$_2$)—(CH$_2$)$_3$—, —C(O)—NH—CH(NH$_2$)—(CH$_2$)$_4$— or —C(O)—NH—C(NH)—NH—(CH$_2$)$_3$—.

According to a preferred embodiment, —X$^4$—(CH$_2$)$_n$— is —C(O)—NH—(CH$_2$)$_4$—.

According to a particular aspect of the invention, —X$^2$—X$^3$—X$^4$— comprises a carbamate functionality —O—C(O)—NH— (e.g. X$^2$ is —O—, X$^3$ is a bond and X$^4$ is —C(O)—NH—, or X$^3$ is —(CH$_2$—CH$_2$—O)$_m$— or —(CH$_2$—O)$_p$— and X$^4$ is —C(O)—NH—).

According to a particular embodiment, the structural element —X$^2$—X$^3$—X$^4$—(CH$_2$)$_n$— comprises from 5 to 12 atoms in the main chain, such as 6, 7, 8, 9, 10 or 11 atoms in the main chain.

According to a particular embodiment, —X$^2$—X$^3$—X$^4$— is —O—C(O)—NH—; —O—CH$_2$—O—C(O)—NH— or —O—(CH$_2$)$_2$—O—C(O)—NH—.

According to a further particular embodiment, —X$^2$—X$^3$—X$^4$— is —X$^2$—CH$_2$—O—C(O)—NH—, wherein X$^2$ is >CH— or >N— wherein the carbon or the nitrogen atom together with two adjacent ring atoms of X$^1$ forms a 3-membered ring; or X$^2$ is —CH$_2$—CH<, —NH—CH< or —CH$_2$—N< wherein the two carbon atoms or the carbon and the nitrogen atom together with two adjacent ring atoms of X$^1$ form a 4-membered ring; or X$^2$ is —CH$_2$—CH$_2$—CH<, —NH—CH$_2$—CH<, —CH$_2$—NH—CH<, —CH$_2$—CH$_2$—N<, —CH$_2$—CH(H)—CH$_2$—, —N(H)—C(H)(H)—CH$_2$— or —CH$_2$—N(H)—CH$_2$— wherein the three carbon atoms or the two carbon atoms and the nitrogen atom together with two adjacent ring atoms of X$^1$ form a 5-membered ring.

According to a preferred embodiment, X$^1$—X$^2$—X$^3$—X$^4$—(CH$_2$)— is X$^1$—O—C(O)—NH—(CH$_2$)$_4$—, X$^1$—O—CH$_2$—O—C(O)—NH—(CH$_2$)$_4$— or X$^1$—O—(CH$_2$)$_2$—O—C(O)—NH—(CH$_2$)$_4$—, wherein X$^1$ is as defined herein and preferably is unsubstituted cyclooctynyl or unsubstituted trans-cyclooctenyl.

According to a further particular embodiment, X$^1$—X$^2$—X$^3$—X$^4$—(CH$_2$)$_n$— is X$^1$—X$^2$—CH$_2$—O—C(O)—NH—(CH$_2$)$_4$—, wherein X$^2$ is >CH— or >N— wherein the carbon or the nitrogen atom together with two adjacent atoms of X$^1$ forms a 3-membered ring; or X$^2$ is —CH$_2$—CH<, —NH—CH< or —CH$_2$—N< wherein. The two carbon atoms or the carbon and the nitrogen atom together with two adjacent ring atoms of X$^1$ form a 4-membered ring; or X$^2$ is —CH$_2$—CH$_2$—CH<, —NH—CH$_2$—CH<, —CH$_2$—NH—CH<, —CH$_2$—CH$_2$—N<, —CH$_2$—CH(H)—CH$_2$—, —N(H)—C(H)(H)—CH$_2$— or —CH$_2$—N(H)—CH$_2$— wherein the three carbon atoms or the two carbon atoms and the nitrogen atom together with two adjacent ring atoms of X$^1$ form a 5-membered ring.

X$^5$ is hydrogen, C$_1$-C$_6$-alkyl, C$_1$-C$_8$-alkoxy-C$_1$-C$_2$-alkyl, C$_2$-C$_7$-alkanoyloxy-C$_1$-C$_2$-alkyl or C$_2$-C$_7$-alkanoylsulfanyl-C$_1$-C$_2$-alkyl.

According to a particular embodiment, X$^5$ is hydrogen, C$_1$-C$_6$-alkoxymethyl, C$_1$-C$_6$-alkoxyeth-1-yl (especially 1-(C$_1$-C$_6$-alkoxy)eth-1-yl), C$_2$-C$_7$-alkanoyloxymethyl or C$_2$-C$_7$-alkanoylsulfanylethyl.

According to a preferred embodiment, X$^5$ is hydrogen.

With regard to the asymmetric carbon atom carrying R$^1$ the compound of the invention may have S- or R-configuration (according to Cahn-Ingold-Prelog priority rules), with S-configuration being preferred.

According to a preferred embodiment, —(CH$_2$)$_n$—CHR$^1$—C(O)O—X$^5$ has formula wherein R$^1$ and X$^5$ are as defined herein and X$^5$ is in particular hydrogen.

According to a further particular embodiment, the compound or salt of the invention is a compound of any one of formulae Ia, Ib, Ic and Id (Ia)

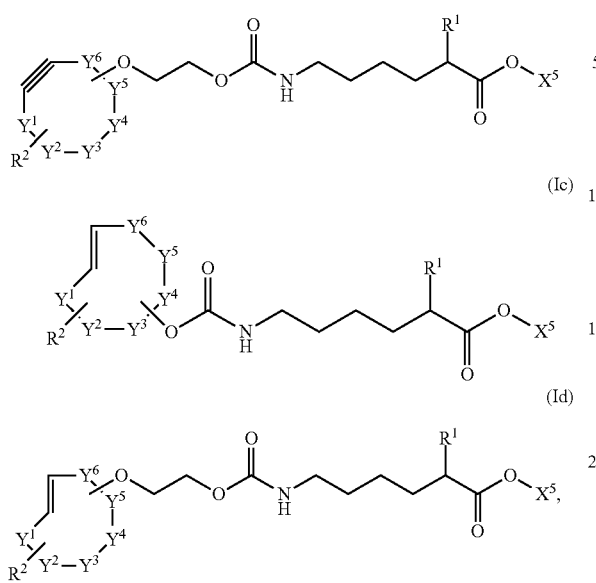

wherein $R^1$, $R^2$, $X^5$, and $Y^1$ to $Y^6$ are as defined herein,
or an acid or base addition salt thereof.

According to a further particular embodiment, the compound or salt of the invention is a compound of formula Ia or Ib, wherein $R^1$, $X^6$, and $Y^1$ to $Y^6$ are as defined herein and $R^2$ is hydrogen or halogen, in particular fluorine, or an acid or base addition salt thereof.

According to a further particular embodiment, the compound or salt of the invention is a compound of formula

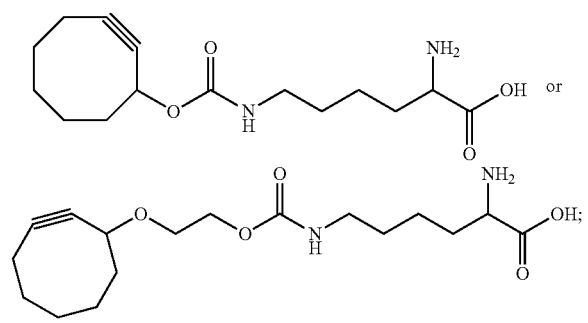

or an acid or base addition salt thereof.

According to a further particular embodiment, the compound or salt of the invention is a compound of formula

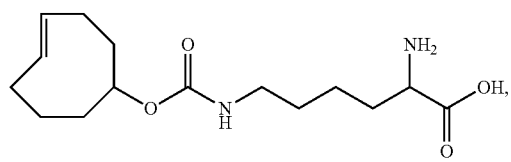 [SMILES: NC(CCCCNC(=O)OC1CC/C=C/CCC1)C(=O)O]

or an acid or base addition salt thereof.

According to a further particular embodiment, the compound or salt of the invention is a compound of formula Ie wherein $R^1$, $R^2$, $X^5$, and $Y^1$ to $Y^6$ are as defined herein and $X^2$ is >CH— or >N— wherein the carbon or the nitrogen atom together with two adjacent ring atoms of $X^1$ forms a 3-membered ring; or $X^2$ is —CH$_2$—CH<, —NH—CH< or —CH$_2$—N< wherein the two carbon atoms or the carbon and the nitrogen atom together with two adjacent ring atoms of $X^1$ form a 4-membered ring; or $X^2$ is —CH$_2$—CH$_2$—CH<, —NH—CH$_2$—CH<, —CH$_2$—NH—CH<, —CH$_2$—CH$_2$—N<,

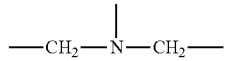

wherein the three carbon atoms or the two carbon atoms and the nitrogen atom together with two adjacent ring atoms of $X^1$ form a 5-membered ring, or an acid or base addition salt thereof.

According to a further particular embodiment, the compound or salt of the invention is a compound of formula

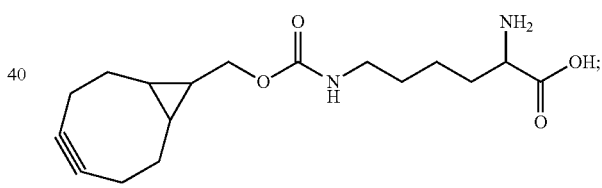

or an acid or base addition salt thereof.

According to a further particular embodiment, the compound or salt of the invention is a compound of formula

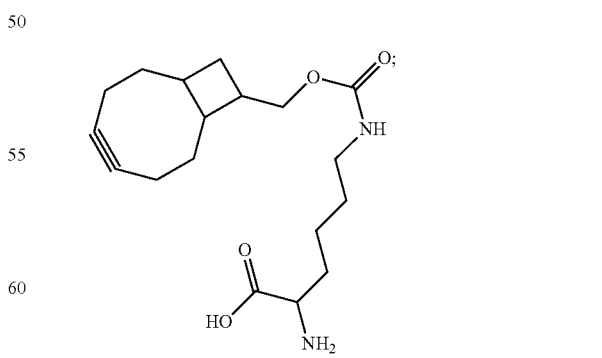

or an acid or base addition salt thereof.

According to one embodiment, the compounds of the invention thus have formula I

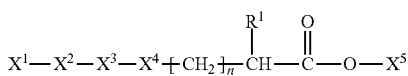
(I)

wherein:
$X^1$ has formula

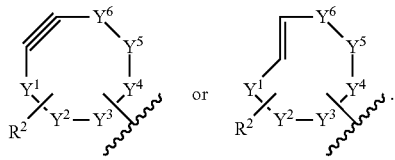

wherein:
$Y^1, Y^2, Y^3, Y^4, Y^5, Y^6$
independently are —$CH_2$—, —NH—, —S— or —O— provided that at least 4 of $Y^1, Y^2, Y^3, Y^4, Y^5, Y^6$ are —$CH_2$—;

$R^2$ is hydrogen, halogen, $C_1$-$C_4$-alkyl, $CF_3$, CN, $C_1$-$C_4$-alkoxy, —O—$CF_3$, $C_2$-$C_5$-alkanoyloxy, $C_1$-$C_4$-alkylaminocarbonyloxy or $C_1$-$C_4$-alkylthio;

$X^2$ is —$CH_2$—, —O—, —S—, —NH—, —C(O)—, —OC(O)—, —C(O)O—, —NH—C(O)— or —C(O)—NH—;

$X^3$ is $C_1$-$C_6$-alkylene, —($CH_2$—$CH_2$—O)$_m$— or a single bond;

$X^4$ is —NH—, —C(O)—NH—, —NH—C(O)—, —NH—CH($NH_2$)—, —CH($NH_2$)—NH—, —NH—C(NH)—NH—, —C(O)—NH—CH($NH_2$)—, —C(O)—NH—C(NH)—NH—, NH—CH($NH_2$)—C(O)— or —NH—C(NH)—NH—C(O)—;

$X^5$ is hydrogen, $C_1$-$C_6$-alkyl, $C_1$-$C_6$-alkoxy-$C_1$-$C_2$-alkyl, $C_1$-$C_7$-alkanoyloxy-$C_1$-$C_2$-alkyl or $C_2$-$C_7$-alkanoylsulfanyl-$C_1$-$C_2$-alkyl;

$R^1$ is —OH or —$NH_2$;
n is an integer from 1 to 4; and
m is an integer from 1 to 6.

According to another embodiment, the compounds of the invention thus have formula I

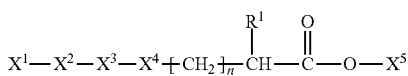
(I)

wherein:
$X^1$ has formula

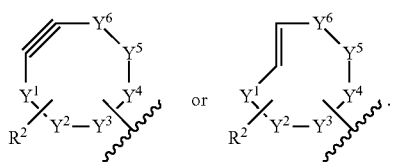

wherein:
$Y^1, Y^2, Y^3, Y^4, Y^5, Y^6$
independently are —$CH_2$—, —NH—, or —O— provided that at least 4 of $Y^1, Y^2, Y^3, Y^4, Y^5, Y^6$ are —$CH_2$—;

$R^2$ is hydrogen, halogen, $C_1$-$C_4$-alkyl, $CF_3$, CN, $C_1$-$C_4$-alkoxy, —O—$CF_3$, $C_2$-$C_5$-alkanoyloxy, $C_1$-$C_4$-alkylaminocarbonyloxy or $C_1$-$C_4$-alkylthio;

$X^2$ is >CH— or >N— wherein the carbon or the nitrogen atom together with two adjacent ring atoms of $X^1$ forms a 3-membered ring, or $X^2$ is —$CH_2$—CH<, —NH—CH< or —$CH_2$—N wherein the two carbon atoms or the carbon and the nitrogen atom together with two adjacent ring atoms of $X^1$ form a 4-membered ring, or $X^2$ is —$CH_2$—$CH_2$—CH<, —NH—$CH_2$—CH<, —$CH_2$—NH—CH<, —$CH_2$—$CH_2$—N<,

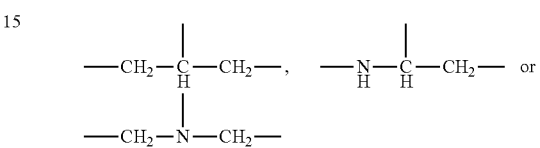

wherein the three carbon atoms or the two carbon atoms and the nitrogen atom together with two adjacent ring atoms of $X^1$ form a 5-membered ring;

$X^3$ is $C_1$-$C_6$-alkylene, —($CH_2$—$CH_2$—O)$_m$—, —($CH_2$—O)$_p$— or a single bond;

$X^4$ is —NH—, —C(O)—NH—, —NH—C(O)—, —NH—CH($NH_2$)—, —CH($NH_2$)—NH—, —NH—C(NH)—NH—, —C(O)—NH—CH($NH_2$)—, —C(O)—NH—C(NH)—NH—, NH—CH($NH_2$)—C(O)— or —NH—C(NH)—NH—C(O)—;

$X^5$ is hydrogen, $C_1$-$C_4$-alkyl, $C_1$-$C_6$-alkoxy-$C_1$-$C_2$-alkyl, $C_2$-$C_7$-alkanoyloxy-$C_1$-$C_2$-alkyl or $C_2$-$C_7$-alkanoylsulfanyl-$C_1$-$C_7$-alkyl;

$R^1$ is —OH or —$NH_2$;
n is an integer from 1 to 4;
m is an integer from 1 to 6; and
p is an integer from 1 to 6.

The acid or base addition salts of the compounds of the invention are especially addition salts with physiologically tolerated acids or bases. Physiologically tolerated acid addition salts can be formed by treatment of the base form of a compound of the invention with appropriate organic or inorganic acids. Compounds of the invention containing an acidic proton may be converted into their non-toxic metal or amine addition salt forms by treatment with appropriate organic and inorganic bases. The compounds and salts of the invention also comprise the hydrates and solvent addition forms thereof, e.g. hydrates, alcoholates and the like.

Physiologically tolerated acids or bases are those which are tolerated by the translation system used for preparation of polypeptides with cyclooctynyl or trans-cyclooctenyl analog groups, e.g. are substantially non-toxic to living, cells.

When compounds or salts of the invention, wherein $X^5$ is other than hydrogen, are used for preparation of polypeptides in a translation system, it is believed that $X^5$ is removed in situ, for example enzymatically within the translation system prior of being incorporated in the polypeptide. Accordingly, $X^5$ is expediently chosen so as to be compatible with the translation system's ability to convert the compound or salts of the invention into, a form that is recognized and processed by the aminoacyl tRNA synthetase.

The compounds and salts of the invention can be prepared by analogy to methods which are well known in the art. Suitable methods for the preparation of compounds of formula (I) are found in the various publications cited herein, all of which are incorporated herein by reference in their entireties. Some methods are outlined herein.

Compounds of the invention comprising a bicyclo[6.1.0]nonynyl group can be prepared from a precursor such as 9-hydroxymethylbicyclo[6.1.0]nonyne that can be synthesized according to Dommerholt et al. (Angew. Chem. Int. Ed. 2010, 49:9422).

The compounds and salts of the invention can be used for preparation of polypeptides comprising one or more than one cyclooctynyl or trans-cyclooctenyl analog group. The invention provides processes for preparing such polypeptides, in vivo or in vitro. In particular, the compounds or salts of the invention can be translationally incorporated in a polypeptide that is encoded by a polynucleotide comprising one or more than one selector codon(s).

The present invention thus also relates to a process for preparing a target polypeptide having one or, more than one cyclooctynyl or trans-cyclooctenyl analog group, the process comprising:
a) providing a translation system comprising:
 (i) an aminoacyl tRNA synthetase, or a polynucleotide encoding it;
 (ii) a compound or salt of the invention;
 (iii) a tRNA having an anticodon to a selector codon, or a polynucleotide encoding said tRNA; and
 (iv) a polynucleotide encoding the target polypeptide and comprising one or more than one selector codon(s),
wherein the aminoacyl tRNA synthetase (i) is capable of specifically acylating the tRNA (iii) with the compound or salt (ii);
b) allowing translation of the polynucleotide (iv); and
c) optionally recovering the resulting polypeptide.

Norbornenyl groups react with 1,2,4,5-tetrazines in a way analogous to trans-cyclooctenyl groups. What is disclosed herein with regard to trans-cyclooctenyl therefore applies in an analogous manner to norbornenyl. Thus, according to a further embodiment, $X^1$ is norbornen-2-yl or norbornen-7-yl, and in particular is norbornen-2-yl.

The term "translation system" refers to the components necessary to incorporate a naturally occurring amino acid in a growing polypeptide chain (protein). Components of a translation system can include, e.g., ribosomes, tRNAs, synthetases, mRNA and the like.

The translation system may be an in vivo or an in vitro translation, system.

An in vitro translation system may be a cell-free translation system. A cell-free translation system is a system for synthesizing a desired protein by obtaining protein factors required for mRNA translation, e.g., in form of a cell extract, followed by reconstituting this reaction in vitro. Such cell-free systems and their use for protein synthesis are known in the art. Examples include extracts of E. coli, wheat germ extract, or rabbit reticulocyte lysate (Spirin and Swartz, Cell-free Protein Synthesis, Wiley VCH Verlag, Weinheim, Germany, 2008).

Preferably, translation system used in the process of the invention is an in vivo translation system. An in vivo translation system can be a cell, e.g. a prokaryotic or eukaryotic cell. The cell can be a bacterial cell, e.g. E. coli; a fungal cell such as a yeast cell, e.g. S. cerevisiae; a plant cell, or an animal cell such as an insect cell or a mammalian cell, e.g. a HeLa cell. Eukaryotic cells used for polypeptide expression may be single cells or parts of a multicellular organism.

According to a particular embodiment, the translation system is an E. coli cell.

According to a further particular embodiment, the translation system is a mammalian cell, e.g. a HeLa cell.

A translation system useful for preparation of polypeptides of the invention comprises, in particular, an aminoacyl tRNA synthetase, or a polynucleotide encoding it; a compound or salt of the invention; a tRNA having an anticodon to, a selector codon, or a polynucleotide encoding said tRNA; a polynucleotide encoding the polypeptide of the invention and comprising one or more than one selector codon(s).

For example, polynucleotides encoding the aminoacyl tRNA synthetase, the tRNA and the polypeptide of the invention may be introduced into a cell by transfection/transformation known in the art.

An aminoacyl tRNA synthetase (RS) is an enzyme capable of acylating a tRNA with an amino acid or amino acid analog. Expediently, the RS used in processes of the invention is capable of acylating a tRNA with the unnatural amino acid of the invention.

The processes of the invention expediently utilize a tRNA aminoacyl tRNA synthetase (tRNA/RS) pair. Preferably, the tRNA/RS pair used in the processes of the invention is orthogonal to the translation system.

The term "orthogonal" as used herein refers to a molecule (e.g., an orthogonal tRNA (O-tRNA) and/or an orthogonal aminoacyl tRNA synthetase (O—RS)) that is used with reduced efficiency by a translation system of interest (e.g., a cell). Orthogonal refers to the inability or reduced efficiency, e.g., less than 20% efficient, less than 10% efficient, less than 5% efficient, or e.g., less than 1% efficient, of an orthogonal tRNA or an orthogonal aminoacyl tRNA synthetase to function with the endogenous aminoacyl tRNA synthetases or, endogenous tRNAs of the translation system of interest.

For example, an orthogonal tRNA in a translation system of interest is acylated by any endogenous aminoacyl tRNA synthetase of a translation system of interest with reduced or even zero efficiency, when compared to acylation of an endogenous tRNA by the endogenous aminoacyl tRNA synthetase. In another example, an orthogonal aminoacyl tRNA synthetase acylates any endogenous tRNA in the translation system of interest with reduced or even zero efficiency, as compared to acylation of the endogenous tRNA by an endogenous aminoacyl tRNA synthetase.

Orthogonal tRNA/RS pairs used in processes of the invention preferably have following properties: the O-tRNA is preferentially acylated with the unnatural amino acid of the invention by the O—RS. In addition, the orthogonal pair functions in the translation system of interest, e.g., the translation system. Uses the unnatural amino acid acylated O-tRNA to incorporate the unnatural amino acid of the invention in a polypeptide chain. Incorporation occurs in a site specific manner, e.g., the O-tRNA recognizes a selector codon, e.g., an amber stop codon, in the mRNA coding for the polypeptide.

The term "preferentially acylates" refers to an efficiency of, e.g., about 50% efficient, about 70% efficient, about 75% efficient, about 85% efficient, about 90% efficient, about 95° i° efficient; or about 99% or more efficient, at which an O—RS acylates an O-tRNA with an unnatural amino acid compared to an endogenous tRNA or amino acid of a translation system of interest. The unnatural amino acid is then incorporated in a growing polypeptide chain with high fidelity, e.g., at greater than about 75% efficiency for a given selector codon, at greater than about 80% efficiency for a given selector codon, at greater than about 90% efficiency for a given selector codon, at greater than about 95% efficiency for a given selector codon, or at greater than about 99% or more efficiency for a given selector codon.

The term "selector codon" refers to codons recognized by the O-tRNA in the translation process and not recognized by an endogenous tRNA. The O-tRNA anticodon loop recognizes the selector codon on the mRNA and incorporates its amino acid, e.g., an unnatural amino acid, at this site in the polypeptide. Selector codons can include, e.g., nonsense codons, such as stop codons, e.g., amber, ochre, and opal codons; four or more base codons; codons derived from natural or unnatural base pairs and the like. For a given system, a selector codon can also include one of the natural three base codons (i.e. natural triplets), wherein the endogenous system does not use said natural triplet, e.g., a system that is lacking a tRNA that recognizes the natural triplet or a system wherein the natural triplet is a rare codon.

An anticodon has the reverse complement sequence of the corresponding codon.

An O-tRNA/O—RS pair is composed of an O-tRNA, e.g., a suppressor tRNA, or the like, and an O—RS.

A suppressor tRNA is a tRNA that alters the reading of a messenger RNA (mRNA) in a given translation system. A suppressor tRNA can read through, e.g., a stop codon, a four base codon, or a rare codon.

The O-tRNA is not acylated by endogenous synthetases and is capable of decoding a selector codon, as, described herein. The O—RS recognizes the O-tRNA, e.g., with an extended anticodon loop, and preferentially acylates the O-tRNA with an unnatural amino acid.

The tRNA and the RS used in the processes of the invention can be naturally occurring or can be derived by mutation of a naturally occurring tRNA and/or RS from a variety of organisms. In various embodiments, the tRNA and RS are derived from at least one organism. In another embodiment, the tRNA is derived from a naturally occurring or mutated naturally occurring tRNA from a first organism and the RS is derived from naturally occurring or mutated naturally occurring RS from a second organism.

A suitable tRNA/RS pair may be selected from libraries of mutant tRNA and RS, e.g. based on the results of a library screening. Alternatively, a suitable tRNA/RS pair may be a heterologous tRNA/synthetase pair that is imported from a source species into the translation system. Preferably, the cell used as translation system is different from said source species.

Methods for evolving tRNA/RS pairs are described, e.g., in WO 02/085923 and WO 02/06075.

Preferably, the RS is a pyrrolysyl tRNA synthetase (pylRS) capable of acylating a tRNA with the unnatural amino acid of the invention.

The pyrrolysyl tRNA synthetase used in processes of the invention may bei wildtype or a genetically engineered pylRS. Examples for wildtype pylRS include, but are not limited to pylRS from archaebacteria and eubacteria such as *Methanosarcina maize, Methanosarcina barkeri, Methanococcoides burtonii, Methanosarcina acetivorans, Methanosarcina thermophila*, and *Desulfitobacterium hafniense*.

Genetically engineered pylRS have been described, for example, by Neumann et al. (Nat Chem Biol 4:232, 2008), by Yanagisawa et al. (Chem Biol 2008, 15:1187), and in EP2192185A1).

According to a particular embodiment, the pyrrolysyl tRNA synthetase used for preparation of polypeptides of the invention is wildtype pyrrolysyl tRNA synthetase from *M. maize*.

According to a particular embodiment, the pyrrolysyl tRNA synthetase comprises the amino acid sequence of wildtype *M. maize* pyrrolysyl tRNA synthetase set forth in SEQ ID NO:1, or a functional fragment thereof.

```
SEQ ID NO: 1:
MDKKPLNTLISATGLWMSRTGTIHKIKHHEVSRSKIYIEMACGDHLVVNNSRSSRTARAL    60

RHHKYRKTCKRCRVSDEDLNKFLTKANEDQTSVKVKVVSAFTRTKKAMPKSVARAPKFLE    120

NTEAAQAQPSGSKFSPAIPVSTQESVSVPASVSTSISSISTGATASALVKGNTNPITSMS    180

APVQASAPALTKSQTDRLEVLLNPKDEISLNSGKPFRELESELLSRRKKDLQQIYAEERE    240

NYLGKLEREITRFFVDRGFLEIKSPILIPLEYIERMGIDNDTELSKQIFRVDKNFCLRPM    300

LAPNLYNYLRKLDRALPDPIKIFEIGPCYRKESDGKEHLEEFTMLNFCQMGSGCTRENLE    360

SIITDFLNHLGIDFKIVGDSCMVYGDTLDVMHGDLELSSAVVGPIPLDREWGIDKPWIGA    420

GFGLERLLKVKHDFKNIKRAARSESYYNGISTNL    454
```

According to another particular embodiment, the pyrrolysyl tRNA synthetase is pyrrolysyl tRNA synthetase from *M. maize* comprising one or more than one amino acid alteration, preferably selected from amino acid substitutions Y306A and Y384F.

According to a particular embodiment, the pyrrolysyl tRNA synthetase comprises the amino acid sequence of Mutant *M. maize* pyrrolysyl tRNA synthetase set forth in SEQ. ID NO:2, or a functional fragment thereof.

```
SEQ ID NO: 2:
MDKKPLNTLISATGLWMSRTGTIHKIKHHEVSRSKIYIEMACGDHLVVNNSRSSRTARAL    60

RHHKYRKTCKRCRVSDEDLNKFLTKANEDQTSVKVKVVSAPTRTKKAMPKSVARAPKPLE    120

NTEAAQAQPSGSKFSPAIPVSTQESVSVPASVSTSISSISTGATASALVKGNTNPITSMS    180

APVQASAPALTKSQTDRLEVLLNPKDEISLNSGKPFRELESELLSRRKKDLQQIYAEERE    240

NYLGKLEREITRFFVDRGFLEIKSPILIPLEYIERMGIDNDTELSKQIFRVDKNFCLRPM    300

LAPNLANYLRKLDRALPDPIKIFEIGPCYRKESDGKEHLEEFTMLNFCQMGSGCTRENLE    360
```

```
SIITDFLNHLGIDFKIVGDSCMVFGDTLDVMHGDLELSSAVVGPIPLDREWGIDKPWIGA    420

GFGLERLLKVKHDFKNIKRAARSESYYNGISTNL                              454
```

Any aminoacyl tRNA synthetase described herein may be used for acylation of a tRNA with the compound of the invention.

According to a preferred embodiment, wildtype *M. maize* pyrrolysyl tRNA synthetase is used for acylation of a tRNA with a compound of formula

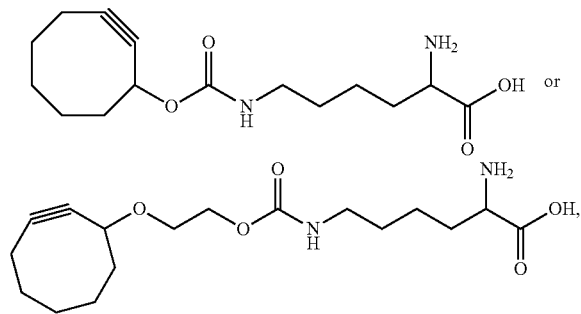

or a salt thereof.

According to a further preferred embodiment, wildtype *M. maize* pyrrolysyl tRNA synthetase is used for acylation of a tRNA with a compound of formula

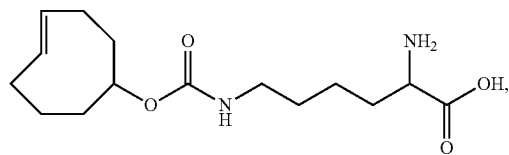 [SMILES: NC(CCCCNC(=O)OC1CC/C=C/CCC1)C(=O)O]

or a salt thereof.

According to another preferred embodiment, a mutant *M. maize* pyrrolysyl tRNA synthetase comprising amino acid substitutions Y306A and Y384F is used for acylation of a tRNA with a compound of formula

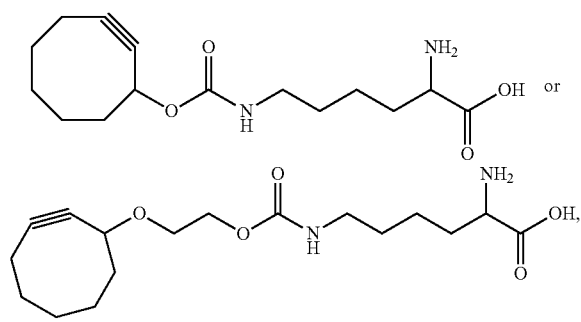

or a salt thereof.

According to further preferred embodiment, a mutant. *M. maize* pyrrolysyl tRNA synthetase comprising amino acid substitutions Y306A and Y384F is used for acylation of a tRNA with a compound of formula

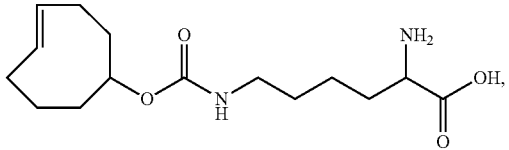 [SMILES: NC(CCCCNC(=O)OC1CC/C=C/CCC1)C(=O)O]

or a salt thereof.

According to further preferred embodiment, wildtype *M. maize* pyrrolysyl tRNA synthetase or a mutant *M. maize* pyrrolysyl tRNA synthetase comprising amino acid substitutions Y306A and Y384F is used for acylation of a tRNA with a compound of formula

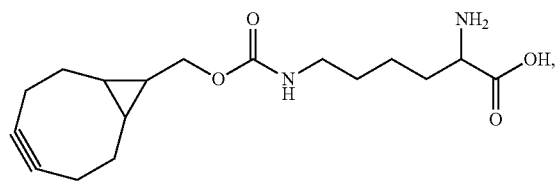 [SMILES: NC(CCCCNC(=O)OCC1C2CCC#CCCC21)C(=O)O]

or a salt thereof.

The tRNA which is used in combination with the pylRS (tRNA$^{pyl}$) may be a wildtype or a genetically engineered tRNA. Examples for wildtype tRNA$^{pyl}$ include, but are not limited to, tRNAs from archaebacteria and eubacteria, such as mentioned above, which facilitate, translational incorporation of pyrrolysyl residues.

Selector codons utilized in processes of the present invention expand the genetic codon framework of the protein biosynthetic machinery of the translation system used. For example, a selector codon includes, e.g., a unique three base codon, a nonsense codon, such as a stop codon, e.g., an amber codon, or an opal codon, an unnatural codon, at least a four base codon or the like. A number of selector codons, can be introduced into a polynucleotide encoding a desired polypeptide (target polypeptide), e.g., one or more, two or more, more than three, etc.

The 64 genetic codons code for 20 amino acids and three stop codons. Because only one stop codon is needed for translational termination, the other two can in principle be used to encode nonproteinogenic amino acids. The amber stop codon, UAG, has been successfully used in in vitro biosynthetic system and in *Xenopus oocytes* to direct the incorporation of unnatural amino acids. Among the three stop codons, UAG, is the least used stop codon in *E. coli*. Some *E. coli* strains contain natural Suppressor tRNAs, which recognize UAG and insert a natural amino acid. In addition, these amber suppressor tRNAs have been used in conventional protein mutagenesis.

In one embodiment, the methods involve the use of a selector codon that is a stop codon for the incorporation of a compound of the invention. For example, an O-tRNA is generated that recognizes the stop codon, preferably the amber stop codon, and is acylated by an O—RS with a compound of the invention. This O-tRNA is not recognized by the naturally occurring aminoacyl-tRNA synthetases. Conventional site-directed mutagenesis can be used to introduce the stop codon, e.g., the amber stop codon, at the site of interest into the polynucleotide sequence encoding the target polypeptide. When the O—RS, O-tRNA and the mutant gene are combined in a translation system, the unnatural amino acid is incorporated in response to the amber stop codon to give a polypeptide containing the unnatural amino acid analog, i.e. the compound of the invention, at the specified position(s).

The incorporation of the compounds of the invention in vivo can be done without significant perturbation of the host, e.g., an E. coli or HeLa cell. For example, because the suppression efficiency for the amber stop codon depends upon the competition between the O-tRNA, e.g., the amber suppressor tRNA, and the release factor 1 (RF1) (which binds to the amber stop codon and initiates release of the growing peptide from the ribosome), the suppression efficiency can be modulated by, e.g., either increasing the expression level of O-tRNA, e.g., the suppressor tRNA, or by using an RF1 deficient strain.

According to particular embodiment, the tRNA$^{pyl}$ used in processes of the invention comprises the CUA anticodon to the amber stop codon.

Other selector codons useful for encoding compounds of the invention are rare codons. For example, when the arginine concentration in an in vitro protein synthesis reaction is reduced, the rare arginine codon, AGG, has proven to be efficient for insertion of Ala by a synthetic tRNA acylated with alanine. In this case, the synthetic tRNA competes with the naturally occurring tRNA$^{Arg}$, which exists as a minor species in E. coli. Some organisms do not use all triplet codons. For example, an unassigned codon AGA in Micrococcus luteus has been utilized for insertion of amino acids in an in vitro transcription/translation extract. Accordingly, any triplet codon not used by the translation system applied in the processes of the invention can serve as selector codon.

The translation system is kept for a suitable time at conditions which allow formation of the polypeptide of the invention by a ribosome. mRNA that encodes the target polypeptide and comprises one or more than one selector codon is bound by the ribosome. Then, the polypeptide is formed by stepwise attachment of amino acids at positions encoded by codons which are bound the respective aminoacyl tRNAs. Thus, the compound of the invention is incorporated in the target polypeptide at the position(s) encoded by the selector codon(s).

Translation of the target polypeptide by a translation system may be effected by procedures well known in the art. To facilitate efficient translation, the components of the translation system may be mixed. Cells used as translation system are expediently cultured and kept in a suitable expression medium under conditions and for a time suitable to produce the target polypeptide. It may be required to induce expression by addition of a compound, such as arabinose, isopropyl β-D-thiogalactoside (IPTG) or tetracycline that allows transcription of the target polypeptide gene.

Optionally, after translation the polypeptide of the invention may be recovered from the translation system. For this purpose, the polypeptides of the invention can be recovered and purified, either partially or substantially to homogeneity, according to procedures known to and used by those of skill in the art. Standard procedures well known in the art include, e.g., ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. Antibodies made against the unnatural amino acid or the polypeptides of the invention can be used as purification reagents, i.e. for affinity-based purification of the polypeptides.

A variety of purification/protein folding, methods are well known in the art, including, e.g., those set forth in Scopes, Protein Purification, Springer, Berlin (1993); and Deutscher, Methods in Enzymology Vol. 182: Guide to Protein Purification, Academic Press (1990); and the references cited therein.

As noted, those of skill in the art will recognize that, after synthesis, expression and/or purification, polypeptides can possess a conformation different from the desired conformations of the relevant polypeptides. For example, polypeptides produced by prokaryotic systems often are optimized by exposure to chaotropic agents to achieve proper folding. During purification from, e.g., lysates derived from E. coli, the expressed polypeptide is optionally denatured and then renatured. This is accomplished, e.g., by solubilizing the proteins in a chaotropic agent such as guanidine HCl. In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are well known to those of skill in the art. Polypeptides can be refolded in a redox buffer containing, e.g., oxidized glutathione and L-arginine.

The invention also provides polypeptides produced by the processes of the invention. Such polypeptides of the invention can be prepared by a process that makes use of a translation system.

The present invention thus also relates to a polypeptide comprising one or more than one residue of formula II

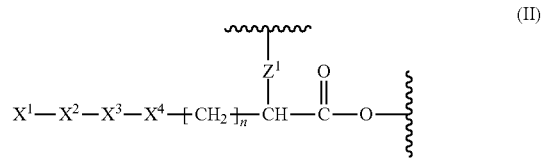 (II)

wherein $X^1$, $X^2$, $X^3$, $X^4$, and n are as defined herein and $Z^1$ is —O— or —NH—.

The cyclooctynyl or trans-cyclooctenyl analog group of the polypeptides of the invention facilitates covalent attachment of a molecule of interest by metal-free click reactions.

Such reactions include cycloadditions of cyclooctynyl analog groups with azides, nitrile oxides, nitrones and diazocarbonyl reagents (Sanders et al., J Am Chem Soc 2010, 133: 949; Agard et. al., J. Am Chem Soc 2004, 126:15046). Nitrile oxides can conveniently be prepared by direct oxidation of the corresponding oximes. Expediently, this oxidation and the cycloaddition of the resulting nitrile oxides with cyclooctynyl analog groups of polypeptides of the invention are performed as a one-pot procedure. Accordingly, suitable molecules of interest for attachment to polypeptides bearing one or more than one cyclooctynyl analog group may have one or more than one azide, nitrile oxide, oxime, nitrone, or diazocarbonyl group.

trans-Cyclooctenyl groups have been reported to effectively react with compounds comprising a 1,2,4,5-tetrazine group by an inverse-electron-demand. Diels-Alder cycloaddition (Devaraj et al., Angew Chem Int Ed Engl 2009, 48:7013). Accordingly, suitable molecules of interest for attachment to polypeptides bearing, one or more than one trans-cyclooctenyl analog group may have one or more than one 1,2,4,5-tetrazine group.

Molecules of interest that can be attached to a polypeptide of the invention include, but are not limited to, a detectable label; a drug; a toxin; a linker; a peptide; a member of a specific binding pair, an epitope tag; and the like.

Detectable labels that can be attached to a polypeptide of the invention include, but are not limited to, fluorescent molecules (e.g., autofluorescent molecules or molecules able to emit fluorescence upon contact with a reagent), spin labels or chromophores for FRET studies (e.g., for studying structure of polypeptides in vivo), radioactive labels (e.g., $^{111}$In, $^{125}$I, $^{131}$I, $^{212}$B, $^{90}$Y, $^{188}$Rh, and the like), biotin (e.g., to be detected through reaction of biotin and avidin), purification tags (other than biotin), and the like. Detectable labels also include peptides or polypeptides that can be detected by antibody binding, e.g., by binding of a detectably labeled antibody or by detection of bound antibody through a sandwich-type assay.

Drugs that can be attached to a polypeptide of the invention include, but are not limited to, cytotoxic compounds (e.g., cancer chemotherapeutic compounds); antiviral compounds; biological response modifiers (e.g., hormones, chemokines, cytokines, interleukins, etc); microtubule affecting agents; hormone modulators; steroidal compounds; and the like.

Specific binding partners that can be attached to a polypeptide of the invention include, but are not limited to, a member of a receptor/ligand pair; a member of an antibody/antigen pair; a member of a lectin/carbohydrate pair; a member of an enzyme/substrate pair; biotin/avidin; biotin/streptavidin; digokin/antidigoxin; and the like.

To facilitate attachment of said molecule of interest it is contacted with a polypeptide of the invention. In many cases, this contacting can be carried out under physiological conditions, i.e. conditions compatible with living cells. The reaction between cyclooctynyl analog group and azide or between cyclooctynyl analog group and nitrile oxide group, respectively, is selective and compatible with aqueous environments. Attachment of the above-described molecules of interest to cyclooctynyl or trans-cyclooctenyl analog groups of the of the invention may be carried out in vitro. For this purpose, the polypeptide of the invention may be purified or provided as part of expression system used for its preparation. Alternatively, the reaction may be carried out in vivo by contacting said molecule of interest with a cell, wherein a polypeptide of the invention has been expressed. In said cell the polypeptide may be located on the cell surface, within the cell membrane or may be intracellular.

Polypeptides of the invention, optionally labeled, phosphorylated, and/or glycosylated, may be used as assay components, e.g. for detection of compounds in bioassays, for therapeutic, prophylactic or cosmetic treatments or as immunogens for antibody production. For such purposes the polypeptides may be applied in purified form or provided as part of the expression system used for its preparation.

The compounds and salts of the invention may be part of a kit for preparing a polypeptide with one or more cyclooctynyl or trans-cyclooctenyl analog groups.

The present invention thus further relates to kits for preparing a polypeptide having one or more than one cyclooctynyl or trans-cyclooctenyl analog group (target polypeptide). The kits comprise a compound or salt of the invention and optionally one or more means for preparing the polypeptide. Such means include, but are not limited to i) an aminoacyl tRNA synthetase, or a polynucleotide encoding it;

ii) a tRNA as described herein, or a polynucleotide encoding it.

Both the aminoacyl tRNA synthetase and the tRNA may, for example, be provided in the form of one or more than one expression vector for said aminoacyl tRNA synthetase and corresponding tRNA.

Such kit may also comprise a polynucleotide encoding a reporter protein, for example an expression vector for, e.g., GFP, wherein the polynucleotide sequence coding for said reporter protein comprises an amber stop codon. Such reporter protein encoding polynucleotide may serve as a positive control to Confirm expression of a polypeptide with cyclooctynyl or trans-cyclooctenyl analog group(s).

Further, such kit may comprise further means for translation of a polynucleotide encoding said polypeptide, for example a translation system, such as E. coli cells, HeLa cells, E. coli extract, wheat germ extract, or rabbit reticulocyte lysate, and instructions for use.

EXAMPLES

Preparation Examples

General Materials and Methods

Unless otherwise noted, materials for chemical synthesis were obtained from commercial suppliers (Sigma-Aldrich, Aldrich, Sigma, Fluka, Acros, Iris) in the highest purity available and used without further purification. Dry solvents were purchased from Sigma-Aldrich, Actos, and Fluka; stored over molecular sieves; and used as supplied. Solvents used for extraction and chromatography were purchased from Fluka, Thermo Fisher Scientific, Merck, and BDH Prolabo (VWR). Flash chromatography (FC) was carried out using. Merck silica gel 60 (63-200 mesh), and thin layer chromatography (TLC) was performed on aluminium-backed, precoated silica gel plates (Macherey-Nagel Alugram Sil G/UV$_{254}$ and Merck silica gel 60 WF$_{254s}$) with cHex/EtOAc or DCM/MeOH/AcOH mixtures as mobile phases. Spots were detected by a UV hand lamp at 254 nm or 366 nm or staining with either A) anisaldehyde staining solution (85 ml EtOH, 10 ml AcOH, 5 ml concentrated H$_2$SO$_4$, 0.5 ml anisaldehyde), B) KMnO$_4$ staining solution (3.0 g KMnO$_4$, 20 µg K$_2$CO$_3$ in 300 ml 5% aqueous NaOH), or C) ninhydrin staining solution (250 ml EtOH, 1.5 ml AcOH, 0.5 g ninhydrin) and subsequent heat treatment. NMR spectra were recorded using a Bruker UltraShield™ Advance 400 (400 MHz, $^1$H; 100 MHz, $^{13}$C) spectrometer and calibrated using residual undeuterated solvent as an internal reference. High-resolution (HR) mass spectra, were recorded at the University of Heidelberg using electrospray ionization (ESI) MS on a Bruker ApexQe hybrid 9.4 T FT-ICR mass spectrometer. Products were characterized by NMR ($^1$H, $^{13}$C) and HR MS.

Example 1

N-ε-(Clyclooct-2-yn-1-yloxy)carbonyl)-L-lysine

N-ε-((Clyclooct-2-yn-1-yloxy)carbonyl)-L-lysine (1) can be prepared as outlined in scheme 1.

Scheme 1: Synthesis of cylcooctyne lysine derivative 1.

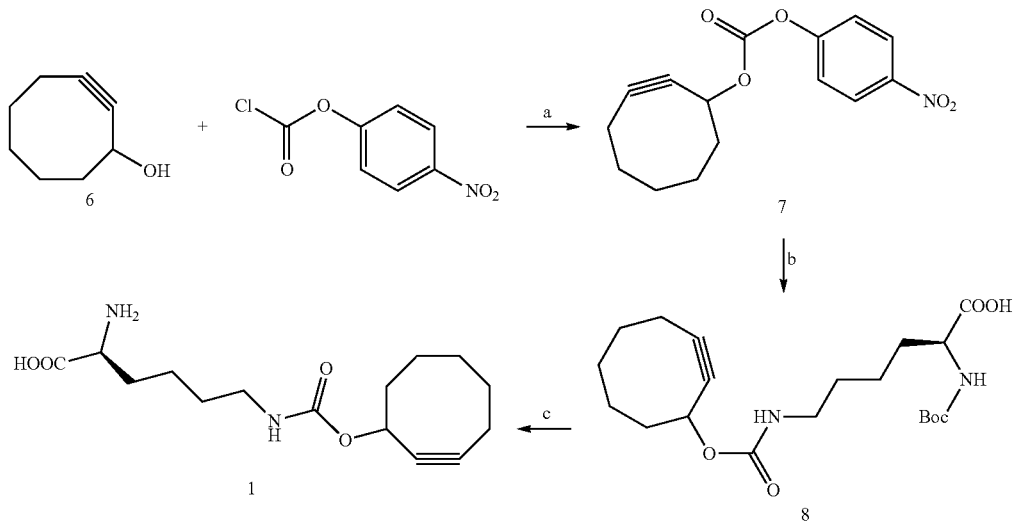

Reagents and conditions: a) TEA, THF, -10° C. to RT, 83%; b) Boc—L-Lys-OH, TEA, DMF, 0° C. to RT, 91%; c) formic acid, CHCl₃, RT, 96%.

Compound 6, cyclooct-2-yn-1-ol was synthesized according to Reese and Shaw (Chem Commun 1970, 1142).

a) Cyclooct-2-yn-1-yl 4-nitrophenyl carbonate (7)

Compound 6 (3.12 g, 25.1 mmol) and TEA (4.20 ml, 30.2 mmol, 1.2 eq) were dissolved in THF (0.2 M, 126 ml) and added dropwise to a stirred solution of 4-nitrophenyl chloroformate (15.20 g, 75.4 mmol, 3.0 eq) and THF (0.7 M, 36 ml) over a period of 1 h at −10° C. The reaction mixture was allowed to warm up to RT and stirred overnight. Then cHex (100 ml) was added and the THF was removed under reduced pressure. Filtration of the mixture followed by FC (cHex:EtOAc 9:1) gave 7 as a yellow oil (6.03 g, 20.9 mmol, 83%). $R_f$(cHex/EtOAC 4:1)=0.70.

$^1$H-NMR (CDCl₃) δ=>8.28 (dt, $^3J$=9.30, $^3J$=2.72, 2H, CH$^{aromatic}$), 7.40 (dt, $^3J$=9.30, $^3J$=2.72, 2H, CH$^{aromatic}$), 5.30-5.35 (m, 1H, CH$^{propargyl}$), 2.10-2.38 (m, 3H, CH$_2^{ring}$), 1.92-1.99 (m, 2H, CH$_2^{ring}$), 1.74-1.88 (m, 3H, CH$_2^{ring}$), 1.59-1.64 (m, 2H, CH$_2^{ring}$) ppm.

b) N-α-tert-Butyloxycarbonyl-N-ε-((cyclooct-2-yn-1-yloxy)carbonyl)-L-lysine (8)

Compound 7 (0.93 g, 3.21 mmol) was dissolved in DMF (0.2 M, 16 ml) and added dropwise to a stirred solution of Boc-L-Lys-OH (1.03 g, 4.18 mmol, 1.3 eq) and TEA (1.35 ml, 9.64 mmol, 3.0 eq) in DMF (0.5 M, 6 ml) over a period of 1 h at 0° C. The reaction mixture was stirred at RT overnight. After removal of all volatile components by evaporation under reduced pressure, the residue was taken up in H₂O (100 ml) and EtOAc (100 ml). The aqueous phase was acidified with concentrated. HCl, and extracted with EtOAc (3×50 ml). The combined organic layers were washed with saturated NaCl solution and dried over Na₂SO₄. The solvent was evaporated under reduced pressure and the crude product was purified by FC (DCM/MeOH/AcOH 97:2:1) to yield 8 as a very viscous yellow oil (1.17 g, 2.94 mmol, 91%). $R_f$(DCM/MeOH/AcOH 97:2:1)=0.45.

$^1$H-NMR (CDCl₃) δ=5.26-5.32 (m, 1H, CH$^{propargyl}$), 5.19-5.25 (m, 1H, NH), 4.80-4.86 (m, 1H, NH), 4.24-4.34 (m, 1H, α-CH$^{Lys}$), 3.16 (q, $^3J$=6.32, 2H, ε-CH$_2^{Lys}$), 2.10-2.31 (m, 3H, CH$^{ring}$), 1.63-2.04 (m, 9H, CH$_2^{ring}$, CH$_2^{Lys}$), 1.49-1.57 (m, 4H, CH$_2^{Lys}$), 1.45 (s, 9H, Boc) ppm.

$^{13}$C-NMR (CDCl₃) δ=176.5 (C(O)O₂), 156.1 (C$^{Lys}$), 154.7 (C$^{Boc}$), 101.6, 91.2 (2×C$^{ring}$), 80.1 (C(CH₃)₃$^{Boc}$), 67.1 (CH$^{propargyl}$), 53.3 (α-CH$^{Lys}$), 41.9 (CH$_2^{ring}$), 40.5 (ε-CH$_2^{Lys}$), 34.2 (CH$_2^{ring}$), 31.9 (CH$_2^{Lys}$), 29.7 (CH$_2^{ring}$), 29.3 (CH$_2^{Lys}$), 28.5 (3×CH$_3^{Boc}$), 26.2 (CH$_2^{ring}$), 22.4 (CH$_2^{Lys}$), 20.7 (CH$_2^{ring}$) ppm.

c) N-ε-((Cyclooct-2-yn-1-yloxy)carbonyl)-L-lysine (1)

Compound 8 (1.24 g, 3.13 mmol) was dissolved in 70% formic acid in CHCl₃ (0.2 M, 16 ml) and stirred for 36 h at RT. DMF (0.2 M, 16 ml) was added and all volatile components were removed under reduced pressure. The residual was taken up in 0.1 M HCl (100 ml) and lyophilized affording pure HCl salt of 1 as a yellow solid (1.00 g, 3.01 mmol, 96%).

$^1$H-NMR (DMSO-d₆) δ=7.43-7.79 (m, 2H, α-NH₂), 7.18 (t, $^3J$=5.72, 1H, ε-NH), 5.09-5.13 (m, 1H, CH$^{propargyl}$), 3.05 (1, $^3J$=5.72, 1H, α-CH$^{Lys}$), 2.90 (q, $^3J$=5.87, 2H, ε-CH$_2^{Lys}$), 2.00-2.26 (m, 3H, CH$_2^{ring}$), 1.77-1.91 (m, 3H, CH$_2^{ring}$), 1.63-1.71 (m, 2H, CH$_2^{ring}$), 1.41-1.59 (m, 4H, CH$_2^{ring}$, CH$_2^{Lys}$), 1.23-1.37 (m, 4H, CH$_2^{Lys}$) ppm.

$^{13}$C-NMR (DMSO-d₆) δ=170.8 (C(O)O₂), 155.7 (C$^{Lys}$), 101.2, 92.4 (2×C$^{ring}$), 66.0 (CH$^{propargyl}$), 54.4 (α-CH$^{Lys}$), 42.1 (CH$_2^{ring}$), 40.6 (ε-CH$_2^{Lys}$), 34.3 (CH$_2^{ring}$), 31.1 (CH$_2^{Lys}$), 29.7 (CH$_2^{ring}$), 29.5 (CH$_2^{Lys}$), 26.3 (CH$_2^{ring}$), 22.8 (CH$_2^{Lys}$), 20.4 (CH$_2^{ring}$) ppm.

HR-ESI MS: [M+H]⁺ calculated: 297.18088, [M+H]⁺ found: 297.18083; [M+Na]⁺ calculated: 319.16283, [M+Na]⁺ found: 319.16282; [M+K]⁺ calculated: 335.13677, [M+K]⁺ found: 335.13679.

In an alternative procedure for synthesis of compound 1, compound 8 was dissolved in 60% formic acid in CHCl₃. Apart from that, the reaction was performed as described above.

Example 2

N-ε-((2-(Cyclooct-2-yn-1-yloxy)ethoxy)carbonyl)-L-lysine

N-ε-((2-(Cyclooct-2-yn-1-yloxy)ethoxy)carbonyl)-L-lysine (2) can be prepared as outlined in scheme 2.

Scheme 2: Synthesis of cyclooctyne lysine derivative 2.

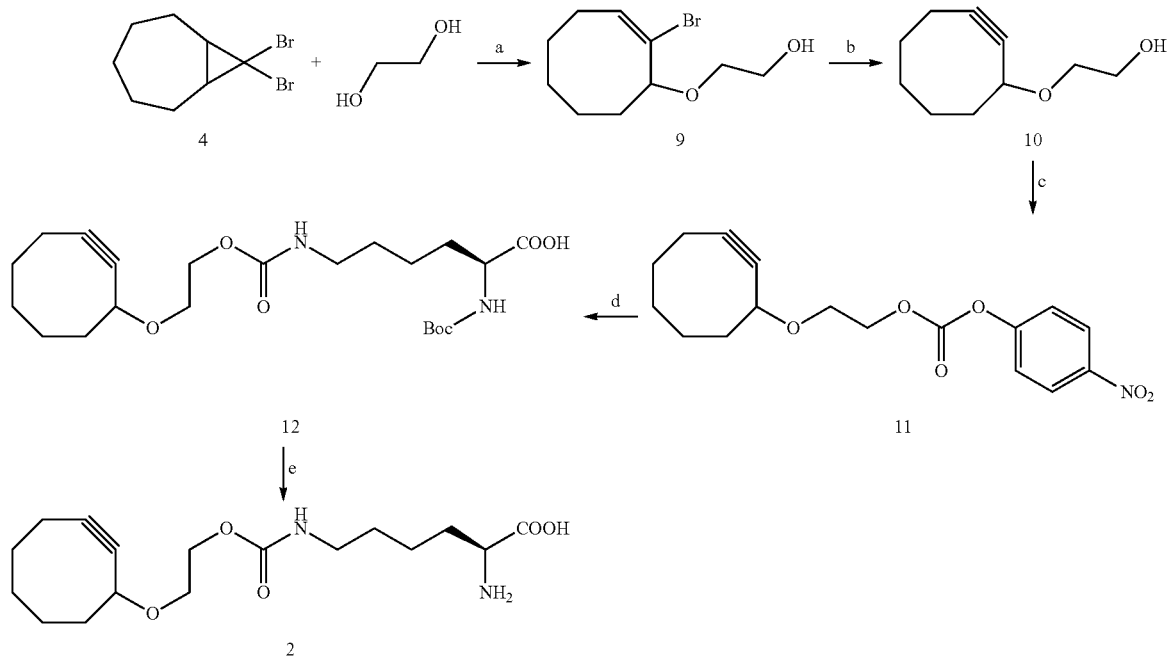

Reagents and conditions: a) AgClO₄, acetone, RT, dark, 49%; b) DBU, DMSO, 60° C., 74%; c) 4-nitrophenyl chloroformate, TEA, THF, -10° C. to RT, 65%; d) Boc—L-Lys-OH, TEA, DMF, 0° C. to RT, 79%; e) formic acid, CHCl₃, RT, 94%.

Compound 4, 8,8-dibromobicyclo[5.1.0]octane, was synthesized starting from commercially available cis-cycloheptene as reported by Neef and Schultz (Angew Chem Int Ed Engl 2009, 48:1498).

a) 2-(Bromocyclooct-2-en-1-yloxy)ethanol (9)

Compound 4 (3.12 g, 11.6 mmol) and anhydrous ethane-1,2-diol (13.0 ml, 23.3 mmol, 20.0 eq) were dissolved in anhydrous acetone (0.6 M, 19 ml), Anhydrous AgClO₄ (7.24 g, 34.9 mmol, 3.0 eq.) was added in small portions under exclusion of light and stirred at RT for 1 h. After addition of EtOAc (100 ml) and filtration, 1 M HCl (100 ml) was added and the aqueous layer was extracted with EtOAc (3×50 ml). The combined organic layers were washed with 1 M HCl/H₂O/saturated NaCl solution (100 ml each) and dried over Na₂SO₄. The solvent was evaporated under reduced pressure and compound 9 (1.42 g, 5.86 mmol, 49%) was obtained as a yellow oil and used without further purification.

$^1$H-NMR (CDCl₃) δ=6.20 (dd, $^3$J=11.73, $^3$J=4.09, 1H, CH$^{vinyl}$), 3.91 (dd, $^3$J=10.22, $^3$J=5.09, 1H, CH$^{allyl}$), 3.78 (t, $^3$J=4.51, 2H, CH$_2^{ethyl}$), 3.61-3.66 (m, 1H, CHH'$^{ethyl}$), 3.44-3.49 (m, 1H, CHH'$^{ethyl}$), 2.27-2.34 (m, 2H, CH$_2^{ring}$), 1.84-2.06 (m, 2H, CH$_2^{ring}$), 1.67-1.76 (m, 2H, CH$_2^{ring}$), 1.43-1.55 (m, 2H, CH$_2^{ring}$), 1.23-1.34 (m, 2H, CH$_2^{ring}$) ppm.

$^{13}$C-NMR (CDCl₃) δ=132.8 (CBr), 131.7 (CH$^{vinyl}$), 85.0 (CH$^{allyl}$), 69.9, 61.9 (2×CH$_2^{ethyl}$), 39.6, 36.5, 33.3, 28.1, 26.3 (5×CH$_2^{ring}$) ppm.

HR-ESI MS: [M+Na]⁺ calculated: 271.03041, [M+Na]⁺ found: 271.03046; [M+K]⁺ calculated: 287.00435, [M+K]⁺ found: 287.00443.

b) 2-(Cyclooct-2-yn-1-yloxy)ethanol (10)

Compound 9 (3.76 g, 15.1 mmol) was dissolved in DMSO M, 30 Ml) and heated to 60° C. DBU (4.51 ml, 30.2 mmol, 2.0 eq) was added, the resulting solution was stirred for 15 min and more DBU (18.0 ml, 121 mmol, 8.0 eq) was added. The mixture was stirred at 60° C. overnight and then cooled to RT. EtOAc (100 ml) and water (100 ml) were added. After acidification to pH 1 with concentrated HCl, the aqueous phase was extracted with EtOAc (3×50 ml). The combined organic layers were washed with 1 M HCl/saturated NaCl solution (100 ml each), dried over Na₂SO₄ and evaporated under reduced pressure. FC (cHex/EtOAc 9:1) afforded compound 10 (1.89 g, 11.2 mmol, 74%) as a light yellow oil.

$R_f$(cHex/EtOAc 4:1)=0.24.

$^1$H-NMR (CDCl₃) δ=4.20-4.24 (m, 1H, CH$^{propargyl}$), 3.72-3.77 (m, 2H, CH$_2^{ethyl}$), 3.65-3.71 (m, 1H, CHH'$^{ethyl}$), 3.44-3.50 (m, 1H, CHH'$^{ethyl}$), 2.10-2.31 (m, 3H, CH$_2^{ring}$), 1.91-2.03 (m, 2H, CH$_2^{ring}$), 1.78-1.89 (m, 2H, CH$_2^{ring}$), 1.58-1.74 (m, 2H, CH$_2^{ring}$), 1.42-1.51 (m, 1H, CH$_2^{ring}$) ppm.

$^{13}$C-NMR (CDCl₃) δ=100.5, 92.5 (2×C$^{ring}$), 72.8 (CH$^{Propargyl}$), 70.4, 61.9 (2×CH$_2^{ethyl}$), 42.3, 34.3, 29.8, 26.3, 20.7 (5×CH$^{ring}$) ppm.

c) 2-(Cyclooct-2-yn-1-yloxy)ethyl 4-nitrophenyl carbonate (11)

Compound 10 (2.64 g, 15.7 mmol) and TEA (2.63 ml, 18.8 mmol 1.2 eq) dissolved in THF (0.2 M, 79 ml) were added dropwise to a stirred solution of 4-nitrophenyl chloroformate (9.49 g, 47.1 mmol, 3.0 eq) and THF (0.7 M, 22 ml) over a period of 1 h at −10° C. The reaction mixture was stirred overnight at RT and diluted with cHex (100 ml). Then cHex (100 ml) was added and the THF was removed under reduced pressure. Filtration of the reaction mixture followed by FC (cHex:EtOAc 4:1) gave compound 11 as a yellow oil (3.42 g, 10.3 mmol, 65%).

$R_f$(cHex/EtOAc 4:1)=0.44.

$^1$H-NMR (CDCl$_3$) δ=8.28 (dt, 3J=9.18, $^3$J=2.12, 2H, CH$^{aromatic}$), 7.39 (dt, $^3$J=9.18, $^3$J=2.12, 2H, CH$^{aromatic}$), 4.41-4.47 (m, 2H, CH$_2^{ethyl}$), 4.25-4.30 (m, 1H, CH$^{propargyl}$), 3.86-3.92 (m, 1H, CHH'$^{ethyl}$), 3.63-3.69 (m, 1H, CHH'$^{ethyl}$), 2.11-2.32 (m, 3H, CH$_2^{ring}$), 1.91-2.05 (m, 2H, CH$_2^{ring}$), 1.79-1.89 (m, 2H, CH$_2^{ring}$), 1.62-1.73 (m, 2H, CH'$_2^{ring}$), 1.42-1.52 (m, 1H, CH$_2^{ring}$) ppm.

$^{13}$C-NMR (CDCl$_3$) δ=156.5 (C(O)O$_2$), 155.6, 152.5 (2×C$^{aromatic}$), 125.3, 122.3 (2×CH$^{aromatic}$), 101.0, 92.1 (2×C$^{ring}$), 73.0 (CH$^{propargyl}$), 68.5, 66.3 (2×CH$_2^{ethyl}$) 42.3, 34.3, 29.7, 26.3, 20.7 (5×CH$_2^{ring}$) ppm.

d) N-α-tert-Butyloxycarbonyl-N-ε-((2-(cyclooct-2-yn-1-yloxy)ethoxy)carbonyl)-L-lysine (12)

Compound 11 (0.60 g, 1.81 mmol) was dissolved in DMF (0.2 M, 9 ml) and added dropwise to a stirred solution Boc-L-Lys-OH (0.58 g, 2.35 mmol, 1.3 eq) and TEA (0.76 ml, 5.42 mmol, 3.0 eq) in DMF (0.5 M, 4 ml) over a period of 1 h at 0° C. The reaction mixture was stirred at RT overnight. After removal of all volatile components by evaporation under reduced pressure, the residue was taken up in H$_2$O (100 ml) and EtOAc (100 ml). The aqueous phase was acidified with concentrated HCl, and extracted with EtOAc (3×50 ml). The combined organic layers were washed with saturated. NaCl solution and dried over Na$_2$SO$_4$. The solvent was evaporated under reduced pressure and the crude product was purified by FC (DCM/MeOH/AcOH 97:2:1) to yield compound 12 as a very viscous yellow oil (0.631 g, 1.43 mmol, 79%).

$R_f$(DCM/MeOH/AcOH 97:2:1)=0.41.

$^1$H-NMR (CDCl$_3$) δ=5.18-5.23 (m, 1H, NH), 4.79-4.85 (m, 1H, NH), 4.16-4.31 (m, 4H, CH$^{propargyl}$, α-CH$^{Lys}$, CH$_2^{ethyl}$), 3.74-3.81 (m, 1H, CHH'$^{ethyl}$), 3.52-3.60 (m, 1H, CHH'$^{ethyl}$), 3.15-3.26 (m, 2H, ε-CH$_2^{Lys}$), 2.11-2.31 (m, 3H, CH$_2^{ethyl}$), 1.51-2.04 (m, 13H, CH$_2^{ring}$, CH$_2^{Lys}$), 1.45 (s, 9H, Boc) ppm.

$^{13}$C-NMR (CDCl$_3$) δ=175.8 (C(O)O$_2$), 156.7 (C$^{Lys}$), 155.9 (C$^{Boc}$), 100.6, 92.4 (2×C$^{ring}$), 80.2 (C(CH$_3$)$_3^{Boc}$), 72.7 (CH$^{propargyl}$), 67.4, 63.9 (2×CH$_2^{ethyl}$), 53.2 (α-CH$^{Lys}$), 42.2 (CH$_2^{ring}$), 40.5 (ε-CH$_2^{Lys}$), 34.3 (CH$_2^{ring}$), 31.8 (CH$^{Lys}$), 29.8 (CH$_2^{ring}$), 29.3 (CH$_2^{Lys}$), 28.3 (3×CH$_3^{Boc}$), 26.4 (CH$_2^{ring}$), 22.3 (CH$_2^{Lys}$), 20.7 (CH$_2^{ring}$) ppm.

HR-ESI MS: [M+H]$^+$ calculated: 441.25953, [M+H]$^+$ found: 441.25982; [M+Na]$^+$ calculated: 463.24147, [M+Na]$^+$ found: 463.24172; [M+K]$^+$ calculated: 479.21541, [M+K]$^+$ found: 479.21570.

e) N-ε-((2-(Cyclooct-2-yn-1-yloxy)ethoxy)carbonyl)-L-lysine (2)

Compound 12 (2.08 g, 4.71 mmol) was dissolved in 70% formic acid in CHCl$_3$ (0.2 M, 24 ml) and stirred for 36 h at RT. DMF (0.2 M, 24 ml) was added and all volatile components were removed, under reduced pressure. The residual was taken up in 0.1 M HCl (100 nil) and lyophilized, affording the pure HCl salt of 0.2 as a yellow solid (1.50 g, 4.42 mmol, 94%).

$^1$H-NMR (DMSO-d$_6$) δ=7.34-7.65 (m, 2H, α-NH$_2$), 7.14-7.23 (m, 1H, ε-NH), 4.17-4.25 (m, 1H, CH$^{propargyl}$), 3.95-4.07 (m, 2H, CH$_2^{ethyl}$), 3.49-3.60 (m, 1H, CHH'$^{ethyl}$), 3.38-3.43 (m, 1H, CHH'$^{ethyl}$), 3.05 (t, $^3$J=6.03, 1H, α-CH$^{Lys}$), 2.92 (q, $^3$J=6.23, 2H, ε-CH$_2^{Lys}$), 1.98-2.24 (m, 2H, CH$_2^{ring}$), 1.59-1.86 (m, 5H, CH$_2^{ring}$), 1.44-1.57 (m, 3H, CH$_2^{ring}$, CH$_2^{Lys}$), 1.22-1.39 (m, 6H, CH$_2^{ring}$, CH$_2^{Lys}$) ppm.

$^{13}$C-NMR (DMSO-d$_6$) δ=171.2 (C(O)O$_2$), 156.8 (C$^{Lys}$), 100.4, 93.4 (2×C$^{ring}$), 72.3 (CH$^{propargyl}$), 67.5, 65.9 (2×CH$_2^{ethyl}$), 53.6 (α-CH$^{Lys}$), 42.3 (CH$_2^{ring}$), 40.5 (ε-CH$_2^{Lys}$), 34.4 (CH$_2^{ring}$), 30.7 (CH$_2^{Lys}$), 29.8 (CH$_2^{Lys}$), 29.6 (CH$_2^{ring}$), 26.4 (CH$_2^{ring}$), 22.5 (CH$_2^{Lys}$), 20.5 (CH$_2^{ring}$) ppm.

HR-ESI MS: [M+H]$^+$ calculated: 341.20710, [M+H]$^+$ found: 341.20716; [M+Na]$^+$ calculated: 363.18917, [M+Na]$^+$ found: 363.18904.

In an alternative procedure for synthesis of compound 2, compound 12 was dissolved in 60% formic acid in CHCl$_3$. Apart from that, the reaction was performed as described above.

Example 3

Synthesis of Compounds of the Invention Comprising Trans-Cyclooctenyl Analog Groups Synthesis scheme 3:

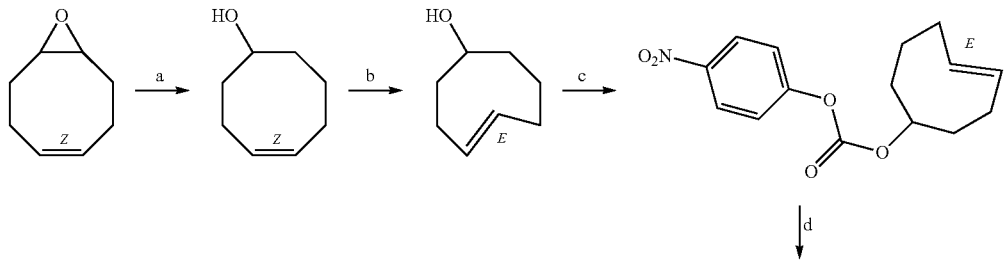

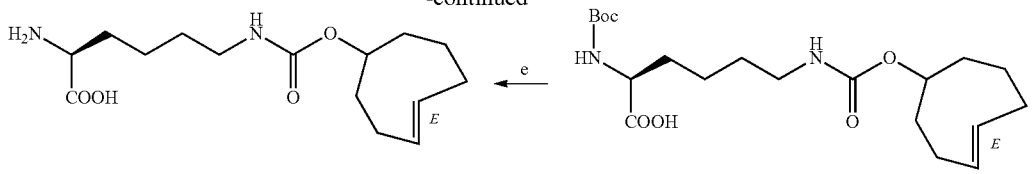

Reaction conditions:
a LiAlH₄, THF, 0° C. to RT, overnight;
b methyl benzoate, diethyl ether, cyclohexane, 254 nm irradiation, RT, 6 h;
c 4-nitrophenyl chloroformate, NEt₃ (TEA), THF, -10° C. to RT, overnight;
d Boc—L-Lys-OH, NEt₃ (TEA), DMF, -10° C. to RT, overnight;
e 70% formic acid in CHCl₃, RT, overnight.
In step (e), 60% formic acid may be used instead of 70% formic acid.

Specific information on synthesis of cyclooctene derivatives can be found in Royzen et al. (J Am Soc 2008, 130:3760) and Hillmyer et. al. (Macromol 1995, 28:6311).

Synthesis scheme 4: Synthesis of trans-cyclooctene lysine derivative 13.

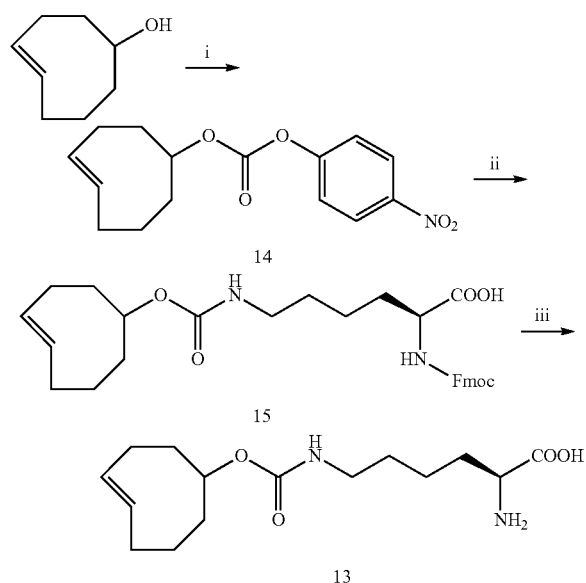

Reagents and conditions: i) 4-nitrophenyl chloroformate, DIEA, THF, 0° C. to RT, 73%; ii) Fmoc—L-Lys-OH, DIEA, DMSO, RT, 85%; iii) 20% piperidine in DMF, RT, 80%. The overall yield after five steps of synthesis starting from (Z)-9-oxabicyclo[6.1.0]non-4-ene was 37% and the average yield per step was 83%.

i) Synthesis of Compound 14:

trans-Cyclooct-4-enol (1.00 g, 7.92 mmol, 1.0 eq.) and DIEA (3.07 g, 4.14 ml, 23.8 mmol, 3.0 eq.) were dissolved in dry THF (0.3 M, 26 ml). The resulting clear solution was added dropwise at 0° C. and under argon to a clear solution of 4-nitrophenyl chloroformate (4.79 g, 23.8 mmol, 3.0 eq.) in dry THF (0.3 M, 26 ml) over a period of 2 h. The reaction mixture was allowed to warm up to RT and stirred overnight. EtOAc (100 ml) was added and insoluble components were filtered off over kieselgur (Celite). The filtrate was then washed with H₂O (50 ml), 1.0 M HCl (50 ml), and saturated NaCl solution (50 ml). Subsequently, the remaining organic phase was dried over Na₂SO₄ and concentrated under reduced pressure. The crude product was purified on silica gel via flash chromatography (Macherey-Nagel silica gel 60, 0.04-0.063 mm, 230-400 mesh; cHex:EtOAc 19:1 v/v). Compound 14 (1.678 g, 5.78 mmol, 73%) was obtained as a white solid.

Major Isomer:

$R_f$(cHex:EtOAc 4:1 v/v)=0.80.

$^1$H-NMR (CDCl₃) δ=8.29-8.24 (m, 2H), 7.39-7.34 (m, 2H), 5.67-5.57 (m, 1H), 5.55-5.45 (m, 1H), 4.48-4.42 (m, 1H), 2.47-2.33 (m, 3H), 2.22-2.07 (m, 2H), 2.05-1.85 (m, 3H), 1.81-1.67 (m, 2H) ppm.

$^1$H-NMR (DMSO-d₆) δ=8.31-8.26 (m, 2H), 7.55-7.50 (m, 2H), 5.66-5.57 (m, 1H), 5.51-5.41 (m, 1H), 4.38-4.32 (m, 1H), 2.36-2.24 (m, 3H), 2.13-2.02 (m, 2H), 1.96-1.86 (m, 2H), 1.85-1.76 (m, 1H), 1.73-1.58 (m, 2H) ppm.

$^{13}$C-NMR (CDCl₃) δ=155.7, 152.0, 145.3, 134.9, 133.0, 125.3, 121.8, 86.4, 40.7, 38.3, 34.1, 32.4, 31.1 ppm.

$^{13}$C-NMR (DMSO-d₆) δ=155.9, 151.9, 145.5, 135.4, 133.1, 125.8, 123.1, 86.2, 40.5, 38.0, 34.0, 32.4, 31.1 ppm.

Minor Isomer:

$^1$H-NMR (CDCl₃)=8.33-8.27 (m, 2H), 7.42-7.38 (m, 2H), 5.69-5.54 (m, 2H), 5.03-4.97 (m, 1H), 2.50-2.27 (m, 4H), 2.23-2.16 (m, 1H), 1.96-1.85 (m, 2H), 1.82-1.71 (m, 1H), 1.67-1.58 (m, 1H), 1.39-1.30 (m, 1H) ppm.

$^{13}$C-NMR (CDCl₃) δ=155.7, 152.0, 145.3, 135.5, 131.5, 125.3, 121.9, 76.0, 40.6, 34.1, 32.1, 29.8, 28.0 ppm.

HR MS (FAB+) m/z: calculated for $C_{15}H_{18}NO_5$ [M+H]⁺: 292.1185, measured: 292.1151.

ii) Synthesis of Compound 15:

Fmoc-L-Lys-OH (0.69 g, 1.87 mmol, 1.2 eq.) was suspended in DIEA (0.24 g, 0.33 ml, 1.87 mmol, 1.2 eq.) and anhydrous DMSO (0.2 M, 8 ml) under argon. To this white suspension, a clear solution of compound 14 (0.45 g, 1.56 mmol, 1.0 eq.) in anhydrous DMSO (0.2 M, 8 ml) was added dropwise at RT and under argon over a period of 2 h. The reaction mixture was stirred for additional 4 h at RT. H₂O (50 ml) and EtOAc (150 ml) were added and the pH of the aqueous layer was adjusted to 1-3 with concentrated HCl. The phases were separated and the aqueous layer was extracted with EtOAc (2×50 ml). The combined organic layers were washed with saturated NaCl solution (2×50 ml) and dried over Na₂SO₄. All volatile components were evaporated under reduced pressure and the crude product was purified by flash chromatography (Macherey-Nagel silica gel 60, 0.04-0.063 mm, 230-400 mesh; DCM:MeOH 95:5 v/v) to yield compound 15 (0.69 g, 1.32 mmol, 85%) as a white solid. To avoid acidic conditions that might lead to an isomerization of the double bond from trans to cis conformation, no AcOH was used for purification.

Major Isomer:

$R_f$(DCM:MeOH:AcOH 96:2:2 v/v/9)=0.16.

$^1$H-NMR (DMSO-d₆) δ=7.87 (d, $^3J$(H,H)=7.4 Hz, 2H), 7.70 (d, $^3J$(H,H)=7.3 Hz, 2H), 7.40 (t, $^3J$(H,H)=7.4 Hz, 2H), 7.31 (t, $^3J$(H,H)=7.4 Hz, 2H), 6.92 (t, $^3J$(H,H)=4.4 Hz, 1H), 5.58-5.47 (m, 1H), 5.44-5.34 (m, 1H), 4.33-4.12 (m, 4H), 3.86-3.73 (m, 1H), 2.96-2.82 (m, 2H), 2.28-2.15 (m, 3H), 1.90-1.76 (m, 4H), 1.69-1.42 (m, 5H), 1.37-1.18 ppm (m, 4H).

$^{13}$C-NMR (DMSO-d$_6$) δ=156.4, 156.2, 144.4, 144.3, 141.2, 135.4, 133.0, 128.1, 127.5, 125.8, 120.6, 79.3, 65.9, 47.2, 41.2, 40.9, 40.5, 38.7, 34.2, 32.6, 31.4, 31.0, 29.7, 23.3 ppm.

iii) Synthesis of Compound 13:

Compound 15 (0.30 g, 0.58 mmol, 1.0 eq.) was dissolved in 20% piperidine in DMF (50 mM, 12 ml) and stirred for 1 h at RT. All volatile components were removed under reduced pressure. The crude product was purified via flash chromatography (Macherey-Nagel silica gel 60, 0.04-0.063 mm, 230-400 mesh; acetone:MeOH:H$_2$O 65:25:10 v/v/v) on silica gel to yield compound 13 (0.14 g, 0.46 mmol, 80%) as a white solid.

Major Isomer:

R$_f$(acetone:MeOH:H$_2$O 65:25:10 v/v/v)=0.53.

$^1$H-NMR (CD$_3$OD) δ=5.65-5.54 (m, 1H), 5.51-5.41 (m, 1H), 4.38-4.21 (m, 1H), 3.52 (dd, $^3$J(H,H)=7.0, 5.2 Hz, 1H), 3.11-3.02 (m, 2H), 2.37-2.25 (m, 3H), 2.01-1.65 (m, 8H), 1.63-1.37 (m, 5H) ppm.

$^{13}$C-NMR (CD$_3$OD)=173.1, 157.4, 134.7, 132.3, 80.2, 54.7, 40.8, 39.9, 38.2, 33.8, 32.1, 30.7, 30.6, 29.2, 22.1 ppm.

HR MS (ESI) m/z calculated for C$_{16}$H$_{27}$N$_2$O$_4$ [M+H]$^+$: 299.19653, measured: 299.19656.

Example 4

Synthesis of Compounds of the Invention Comprising Norbornenyl Group

Synthesis scheme 5: Synthesis of norborene lysine derivatives 16 (a) and 17 (b).

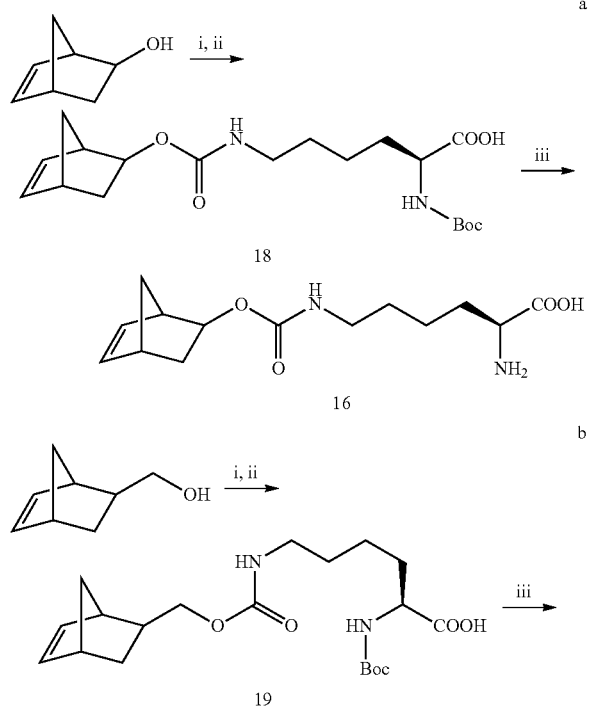

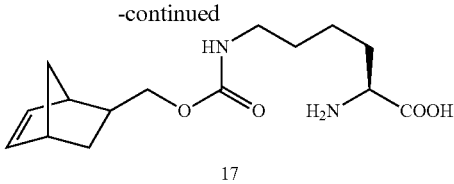

17

Reagents and conditions: (a) i) phosgene, THF, toluene, 0° C. to RT; ii) Boc—L-Lys-OH, THF, NaOH, 97% (after two steps); iii) formic acid, CHCl$_3$, RT, 94%.
(b) i) triphosgene, THF, 0° C. to RT; ii) Boc—L-Lys-OH, THF, NaOH, 0° C. to RT, 96% (after two steps); iii) formic acid, CHCl$_3$, RT, 95%. All norborene starting material was used as supplied as a mixture of endo and exo isomers. No attempts were made to separate the endo and exo isomers at any point of the synthesis. The exo/endo ratio was determined by $^1$H—NMR and is stated in the protocols.

(a) i), ii) Synthesis of Compound 18:

5-Norbornen-2-ol (5.00 g, 45.4 mmol, 1.0 eq.) in dry toluene/THF (1:1 v/v, 1.0 M, 45 ml) was added dropwise at 0° C. and under argon to a 20% solution of phosgene in toluene (8.98 g, 90.8 mmol, 2.0 eq.; 47.8 ml of a 20% solution of phosgene in toluene) over a period of 1 h. The reaction mixture was allowed to warm up to RT and stirred for additional 3 h. Subsequently, all volatile components were removed under reduced pressure and the residue was dried for 30 min in the high vacuum and directly used in the next step. The brown residue was taken up in dry THF (3.5 M, 13 ml) and added dropwise at 0° C. to a solution of Boc-L-Lys-OH (14.5 g, 59.0 mmol, 1.3 eq.) in 1.0 M NaOH/THF (2:1 v/v, 0.3 M, 151 ml). After addition, the reaction mixture was allowed to warm up to RT and stirred for additional 12 h. EtOAc (100 ml) was added and the aqueous layer was acidified to pH<4 with concentrated HCl. The phases were separated and the aqueous layer was extracted with EtOAc (3×70 ml). The combined organic layers were washed with saturated NaCl solution (80 ml) and dried over Na$_2$SO$_4$. All volatile components were evaporated under reduced pressure. The crude product was purified by flash chromatography (Macherey-Nagel silica gel 60, 0.04-0.063 mm, 230-400 mesh; DCM:MeOH:AcOH 96:3:1 v/v/v; co-evaporation with toluene) to yield compound 18 (16.9 g, 44.3 mmol, 97%) as a brown solid in an exo/endo ratio of 3:7 (determined by $^1$H-NMR).

R$_f$(DCM:MeOH:AcOH 90:8:2 v/v/v)=0.45.

$^1$H-NMR (CDCl$_3$) δ=6.34-6.31 (m, 0.7H), 6.25-6.20 (m, 0.3H), 5.99-5.94 (m, 1H), 5.29-5.21 (m, 2H), 4.37-4.24 (m, 1H), 3.22-2.99 (m, 3H), 2.89-2.80 (m, 1H), 2.15-2.08 (m, 0.7H), 1.91-1.66 (m, 3.3H), 1.61-1.37 (m, 14.3H), 1.33-1.23 (m; 1H), 0.99-0.88 ppm (m, 0.7H).

HR MS (ESI) m/z: calculated for C$_{23}$H$_{42}$N$_3$O$_6$ [M+C4H11N+H]$^+$: 456.30681, measured: 456.30678.

(a) iii) Synthesis of Compound 16:

Compound 18 (11.6 g, 30.4 mmol, 1.0 eq.) was dissolved in 60% formic acid in CHCl$_3$ (6:4 v/v, 0.2 M, 152 ml) and stirred for 24 h at RT. DMF (0.2 M, 152 ml) was added and all volatile components were removed under reduced pressure. The residue was taken up in 50 mM HCl and lyophilized, affording pure HCl salt of compound 1 (9.14 g, 28.7 mmol, 94%) as a yellow solid in an exo/endo ratio of 3:7 (determined by $^1$H-NMR).

R$_f$(DCM:MeOH:AcOH 87:10:3 v/v/v)=0.04.

$^1$H-NMR (DMSO-d$_6$) δ=8.47-8.37 (m, 2H), 7.12-7.04 (m, 0.3H), 6.96-6.89 (m, 0.7H), 6.29 (dd, $^3$J(H,H)=5.4, 2.9 Hz, 0.7H), 6.23 (dd, $^3$J(H,H)=5.5, 2.7 Hz, 0.3H), 5.97 (dd, $^3$J(H,H)=5.5, 3.2 Hz, 0.3H), 5.91 (dd, $^3$J(H,H)=5.4, 2.6 Hz, 0.7H), 5.12-5.01 (m, 0.7H), 4.72-4.63 (m, 0.3H), 3.84-3.76 (m, 1H), 3.04-2.98 (m, 0.7H), 2.94-2.86 (m, 2H), 2.81-2.71 (m, 1.3H), 2.29-2.25 (m, 0.3H), 2.05-1.98 (m, 0.7H), 1.79-1.24 (m, 8H), 0.91-0.71 ppm (m, 1H).

¹³C-NMR (DMSO-d₆) δ=171.4, 156.7, 156.6*, 141.3*, 138.6, 133.2*, 132.3, 74.4, 72.7*, 52.2, 47.6, 47.5*, 46.3*, 46.0, 42.2, 40.5*, 34.7, 34.5, 33.7*, 30.0, 29.3, 22.0 ppm (*=signals belonging to exo isomer).

HR MS (ESI) m/z: calculated for $C_{14}H_{23}N_2O_4$ [M+H]⁺: 283.16523, measured: 283.16517.

(b) i), ii) Synthesis of Compound 19:

5-Norbornene-2-methanol (4.17 g, 33.6 mmol, 1.0 eq.) was added dropwise at 0° C. and under argon to a solution of triphosgene (9.96 g, 33.6 mmol, 1.0 eq.) in dry THF (0.5 M, 67 ml) over a period of 2 h and stirred for additional 6 h at 0° C. The reaction mixture was allowed to warm-up to RT and was filtered. Subsequently, all volatile components were removed under reduced pressure and the residue was dried for 1 h in the high vacuum affording the intermediate product as a clear oil which was used, without further purification in the next step. This residue was taken up in dry THF (3.5 M, 10 ml) and slowly added at 0° C. to a solution of Boc-L-Lys-OH (9.93 g, 40.3 mmol, 1.2 eq.) in 1.0 M NaOH/THF (2:1 v/v, 0.3 M, 112 ml). After addition, the reaction mixture was allowed to warm up to RT and stirred for additional 14 h. EtOAc (100 ml) was added and the aqueous layer was acidified to pH<4 with concentrated HCl. The phases were separated and the aqueous layer was extracted with EtOAc (3×70 ml). The combined organic layers were washed with saturated NaCl solution (100 ml) and dried over $Na_2SO_4$. All volatile components were evaporated under reduced pressure. The crude product was purified by flash chromatography (Macherey-Nagel silica gel 60, 0.04-0.063 mm, 230-400 mesh; DCM/MeOH/AcOH 96:3:1 v/v/v, co-evaporation with toluene) to yield compound 19 (12.8 g, 32.3 mmol, 96%) as a yellow solid an exo/endo ratio of 2:3 (determined by ¹H-NMR).

$R_f$(DCM:MeOH:AcOH 90:8:2 v/v/v)=0.44.

¹H-NMR (CDCl₃) δ=6.14 (dd, ³J(H,H)=4.9, 2.7 Hz, 0.6H), 6.11-6.06 (m, 0.8H), 5.94 (dd, ³J(H,H)=5.4, 2.6 Hz, 0.6H), 5.52-5.46 (m, 0.6H), 5.30-5.23 (m, 0.4H), 4.34-4.24 (m, 4.19-4.07 (m, 1H), 3.99-3.80 (m, 1H), 3.69-3.57 (m, 0.6H), 3.23-3.10 (m, 3H), 2.86 (s, 0.6H), 2.84-2.78 (m, 1H), 2.70 (s, 0.4H), 1.92-1.65 (m, 6H), 1.61-1.10 (m, 12H), 1.19-1.10 (m, 0.4H), 0.58-0.50 (m, 0.6H) ppm.

¹³C-NMR (DMSO-d₆) δ=179.5, 161.5, 161.5, 160.8, 142.5, 142.4, 141.4, 141.4, 83.2, 71.6, 58.7, 54.1, 49.8, 48.6, 48.4, 46.9, 46.3, 33.4, 28.1 ppm. HR MS (ESI) m/z: calculated for $C_{20}H_{33}N_2O_6$ [M+H]⁺: 397.23331, measured: 397.23405; calculated for $C_{20}H_{32}N_2NaO_6$ [M+Na]⁺: 419.21526, measured: 419.21607; calculated for $C_{20}H_{32}KN_2O_6$ [M+K]⁺: 435.18920; measured: 435.19006; calculated for $C_{40}H_{65}N_4O_{12}$[2M+H]⁺: 793.45935, measured: 793.46014.

(b) iii) Synthesis of Compound 17:

Compound 19 (1.82 g, 4.60 mmol, 1.0 eq.) was dissolved in 60% formic, acid in CHCl₃ (6:4 v/v, 0.2 M, 23 ml) and stirred for 24 h at RT. DMF (0.2 M, 23 ml) was added and all volatile components were removed under reduced pressure. The residue was taken up in 50 mM. HCl and lyophilized, affording pure HCl salt of compound 17 (1.46 g, 4.37 mmol, 95%) as a white solid in an exo/endo ratio of 2:3 (determined by ¹H-NMR).

$R_f$(DCM:MeOH:AcOH 87:10:3 v/v/v)=0.04.

¹H-NMR (DMSO-d₆) δ=7.11 (t, ³J(H,H)=5.4 Hz, 0.4H), 7.06 (t, ³J(H,H)=5.4 Hz, 0.6H), 6.15 (dd, ³J(H,H)=5.6, 3.0 Hz, 0.6H), 6.10-6.05 (m, 0.8H), 5.91 (dd, ³J(H,H)=5.6, 2.8 Hz, 0.6H), 4.02-3.95 (m, 0.4H), 3.86-3.79 (m, 0.4H), 3.69-3.62 (m, 0.6H), 3.58-3.40 (m, 2.6H), 2.92 (q, ³J(H,H)=5.2 Hz, 2H), 2.81-2.74 (m, 1.6H), 2.64 (s, 0.4H), 2.33-2.24 (m, 0.6H), 1.80-1.53 (m, 3.4H), 1.40-1.26 (m, 3.4H), 1.24-1.18 (m, 1.4H), 1.15-1.11 (m, 0.6H), 0.45 (ddd, ³J(H,H)=11.5, 4.1, 2.5 Hz, 0.6H) ppm.

¹³C-NMR (DMSO-d₆) δ=171.3, 156.8, 156.7*, 137.7, 137.2*, 136.6*, 132.6, 68.0*, 67.5, 53.4, 49.4, 45.1, 43.9, 43.7, 42.2, 41.6*, 38.6*, 38.4, 30.6, 29.5, 29.1, 28.9*, 22.4 ppm (*=signals belonging to exo isomer).

HR MS (ESI) m/z: calculated for $C_{15}H_{25}H_2O_4$ [M+H]⁺: 297.18088, measured: 297.18102.

BIOLOGICAL EXAMPLES

Example A

Expression of GFP Comprising a Cyclooctynyl Residue in *E. coli*

A.1 Plasmids and DNA Constructs

An *E. coli* codon optimized gene for wildtype pyrrolysyl tRNA synthetase (pylRS$^{WT}$) and the corresponding tRNA (tRNA$^{pyl}$) from *M. maize* (purchased froth Mr Gene, Regensburg, Germany) was used to replace the two coding regions for *M. jannaschii* tRNA, synthetase and tRNA in the pEVOL plasmid system described by Young et al. (J Mol Biol. 2010; 395:361) to yield the plasmid pEVOL tRNA$^{pyl}$/pylRS$^{WT}$. Further, a plasmid pEVOL tRNA$^{pyl}$/pylRS$^{AF}$ encoding a mutant pyrrolysyl tRNA synthetase comprising amino acid substitutions Y306A and Y384F (pylRS$^{AF}$) was prepared. For this double mutant, two rounds of standard site-directed mutagenesis were performed to introduce Y306A and Y384F into the codon optimized gene. As for the wildtype (WT), two copies of this gene were then cloned into the pEvolv plasmid to generate the mutant plasmid pEVOL tRNA$^{pyl}$/pylRS$^{AF}$.

A.2 Protein Expression and Purification

For expression of the target protein GFP$^{TAG}$, a pBAD (Invitrogen, Carlsbad, USA) plasmid harboring an N-terminal FLAG tagged GFP with a C-terminal 6-His peptide sequence was prepared, wherein the permissive site 39 contained the amber (TAG) stop codon. *E. coli* Top10 cells were co-transformed with the GFP$^{TAG}$ expression vector and either pEVOL tRNA$^{pyl}$/pylRS$^{WT}$ or pEVOL tRNA$^{pyl}$/pylRS$^{AF}$ and grown at 37° C. in the presence of ampicillin and chloramphenicol. Typically, 0.5 ml of an overnight culture was used to inoculate 50 ml Terrific Broth (TB) medium in a shake flask. Cultures typically grew at 37° C. within 1-2 hours to an $OD_{600}$ between 0.2 and 0.3. Then compound 1 or 2 (stock solution: 80 mM in 0.1 M NaOH) or an equal amount of 0.1 M NaOH (for control experiments) was added to a final concentration of 1 mM. The cultures were further grown to an $OD_{600}$ between 0.4 and 0.6. Then expression was induced by adding arabinose to a final concentration of 0.02% (w/v). After 4-6 h of shaking at 37° C., cultures were harvested by centrifugation. Pellets were resuspended in a 4× phosphate buffered saline (4×PBS pH 8.0) solution containing 1 mM phenylmethylsulfonyl fluoride (PMSF), and cells were lyzed by sonication. The lysate was centrifuged for 1 h at 14,000 g and the supernatant was incubated with 50 µl of Ni-NTA beads (Qiagen, Düsseldorf, Germany). Beads were washed with 10 mM imidazole in 4×PBS and then eluted with buffer containing 500 mM imidazole. Wherever mentioned, washing and/or elution was also carried out in a denaturing 4×PBS buffer containing 6 M guanidinium hydrochloride (pH 8.0). Larger expression approaches used to determine yields more accurately, were scaled up accordingly.

Expression of QFP$^{TAG}$ protein was observed in presence of compound 1 and 2, respectively, compared to a negative control (FIG. 1). GFP$^{TAG}$ expression in cells transfected with the expression vector for tRNA$^{Pyl}$/pylRS$^{AF}$ was higher (absolute yield of about 10 mg GFP$^{TAG \to 1}$ (GFP$^{TAG}$ comprising compound 1) per liter culture) than in cells transfected with the expression vector for tRNA$^{Pyl}$/pylRS$^{WT}$. The bands of the Coomassie stained gel shown FIG. 1b were excised, digested with trypsin and chymotrypsin, and the resulting peptides were analyzed by Mass spectrometry (Orbitrap mass spectrometer, Thermofisher, USA; Mascot algorithm). This analysis confirmed site-specific incorporation of compound 1 or 2, respectively, into GFP$^{TAG}$ (Table 1).

at a scan speed of 400 Hz and a zoom factor of two yielding a final pixel size of 120.1 nm×120.1 nm. In addition to a DIC image the sample was excited using a blue diode laser operating at a wavelength of 405 nm, while simultaneously recording the fluorescence signal in two channels (blue=415-470 nm and green=520-540 nm). Fluorescence in the blue channel originated from clicked compound 3, while fluorescence in the green channel originated from GFP that can be directly excited also at 405 nm and possibly also via energy transfer from clicked compound 3 to the GFP chromophore.

TABLE 1

Mass spectrometry of GFP$^{TAG \to 1}$ and GFP$^{TAG \to 2}$ bands from gel shown in FIG. 1b.

| | protease | Monoisotopic Mass (calc) [Da] | Match mass, found [Da] | Δ mass | Ion score | Peptide Sequence (X = Amber TAG site) |
|---|---|---|---|---|---|---|
| GFP$^{TAG \to 1}$ | chymotrypsin | 1583.76788 | 1583.76788 | (−)0.00003 | 76 | SVSGEGEGDATXGKL |
| GFP$^{TAG \to 1}$ | trypsin | 1617.75224 | 1617.75224 | (−)0.00005 | 84 | FSVSGEGEGDATXKG |
| GFP$^{TAG \to 2}$ | chymotrypsin | 1627.79410 | 1627.79410 | (−)0.00007 | 31 | SVSGEGEGDATXGKL |
| GFP$^{TAG \to 2}$ | trypsin | 1661.77846 | 1661.77846 | 0.00008 | 39 | FSVSGEGEGDATXGK |

Example B

Fluorescence Labeling of GFP$^{TAG \to 1}$ Within Living E. coli Cells

B.1 In Vivo Labeling of Cyclooctynyl Comprising GFP by Fluorogenic Azido Coumarin GFP$^{TAG \to 1}$ was expressed in E. coli harboring tRNA$^{Pyl}$/pylRS$^{AF}$ in the presence of 1 mM compound 1. Four to six hours after induction of expression, a 5 ml sample of culture was harvested. The cells were washed two times with 12 ml PBS, resuspended in 12 ml PBS, incubated for 1 h at 4° C. in the dark, and washed another two times with 12 ml PBS. Then cells were pelleted, resuspended in 3 ml PBS (OD$_{600}$~2-3) containing 50 µM azido coumarin (compound 3; commercially available from Base Click; can be synthesized according to Sivakumar et al., Org Lett 2004, 6:4603), and incubated shaking at 37° C. in the dark.

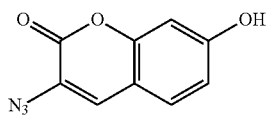

3

A control experiment was performed by repeating the same imaging procedure with cells expressing GFP$^{WT}$. In this construct, the synthetase and tRNA are still active in recognizing compound 1, but GFP$^{WT}$ contains no amber stop codon that allows incorporation of compound 1.

B.2 Analysis of Labeled GFP Via Fluorescence Microscopy

After 4-6 h incubation with compound 3, 5 ml cells were harvested, washed two times with 1.5 ml PBS, resuspended in PBS, incubated for 1 h at 4° C. in the dark, washed another two times with 1.5 ml PBS, and then allowed to settle on a coverslip. Cells were mounted on Leica SP5 microscope employing a 1.4 NA oil objective (Leica, Mannheim, Germany). Images containing 1.024*1024 pixels were acquired The same emission channels were recorded during excitation with an argon ion laser operating at λ=488 nm, which only excites GFP. Relative fluorescence intensities are summarized in Table 2. When excited at $\lambda_{ex}$=405 nm, cells expressing GFP$^{TAG \to 1}$ showed fluorescence in the blue as well as in the green channel indicating the presence of clicked compound 3 as well as of the GFP chromophore. In contrast, in the control cells expressing GFP$^{WT}$ only background fluorescence was visible in the blue channel at $\lambda_{ex}$=405 nm, i.e. no compound 3 was detected in these cells. The GFP fluorescence observed in the green channel was stronger in the control cells than in cells expressing GFP$^{TAG \to 1}$, since GFP$^{WT}$ naturally expresses better than the amber suppressed GFP$^{TAG \to 1}$. In summary, fluorescence in the blue channel in GFP$^{TAG \to 1}$ expressing cells was about two to three-times higher than background, verifying that coupling with compound 3 occurred in vivo.

TABLE 2

Fluorescence intensity of E. coli cells harboring labeled GFP$^{TAG \to 1}$

| | $\lambda_{em}$ = 415-470 nm | $\lambda_{em}$ = 510-540 nm | |
|---|---|---|---|
| $\lambda_{ex}$ = 405 nm | +++ | +++ | GFP$^{TAG \to 1}$ |
| $\lambda_{ex}$ = 488 nm | − | + | |
| $\lambda_{ex}$ = 405 nm | + | ++++ | GFP$^{WT}$ (control) |
| $\lambda_{ex}$ = 488 nm | − | +++ | |

Fluorescence intensity: − (no fluorescence), + (weak), ++ (moderate), +++ (strong), ++++ (very strong)

B.3 Analysis of Labeled GFP Via SDS-PAGE

Figure 3:
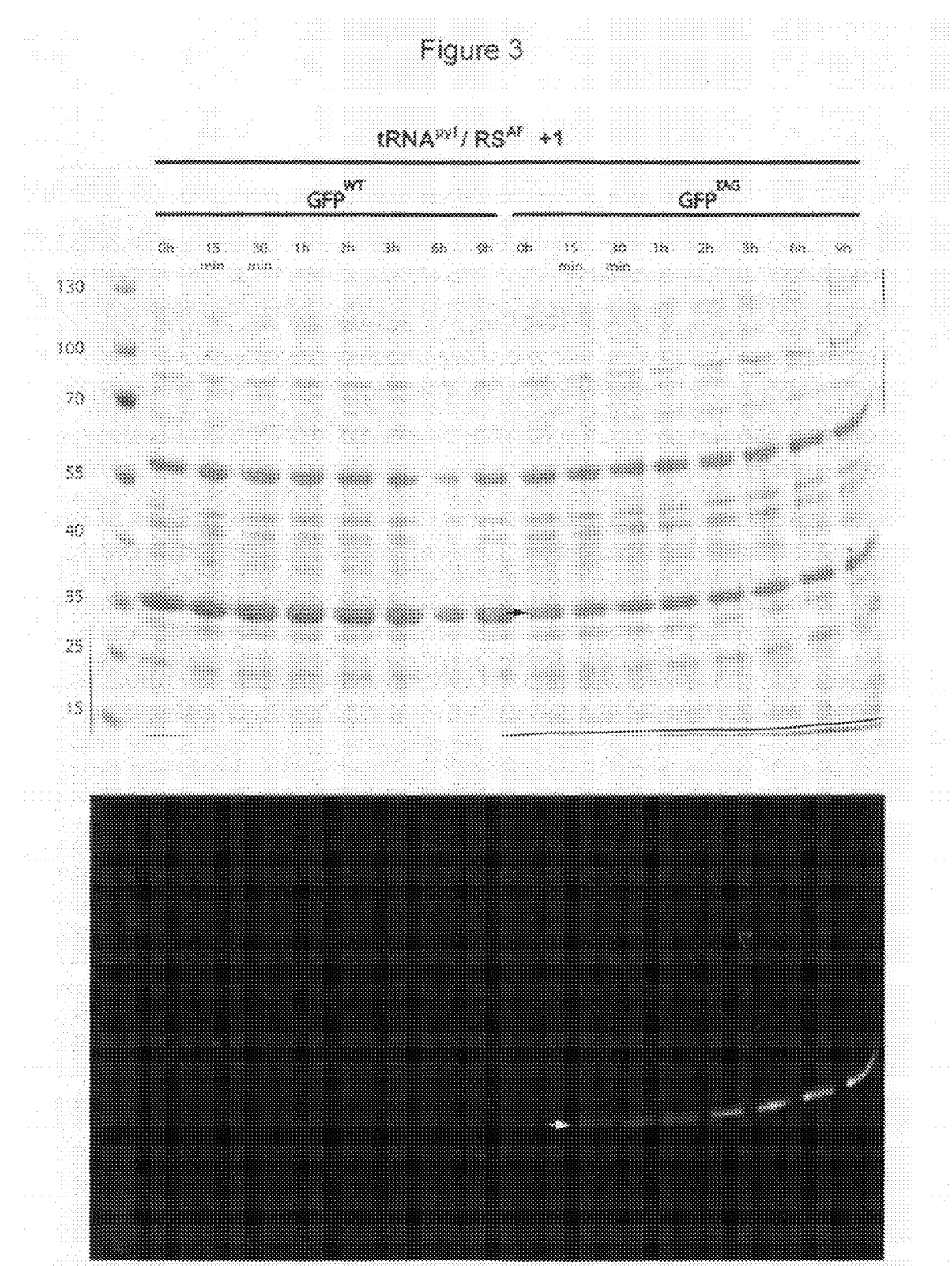
FIG. 3 shows whole cell lysate analysis of *E. coli* cultures described in example B. After adding fluorogenic azido coumarin (compound 3) to cultures expressing $GFP^{TAG \to 1}$ and $GFP^{WT}$, small samples were taken at the indicated time points and subjected to SDS-PAGE. After-electrophoresis, a fluorescent image of the gel (a) was taken at an excitation wavelength 365 nm by detecting the emission with an ethidium bromide filter setting. The proteins separated in the SDS polyacrylamide were visualized by Coomassie staining (b). The GFP running height is indicated with an arrow. Sizes of marker proteins are given in kDa.

Coupling of compound 3 to cyclooctynyl comprising GFP was also confirmed by analyzing fluorescence in cell lysate by SDS-PAGE. After adding compound 3 to the E. coli cultures expressing GFP$^{TAG \to 1}$ or GFP$^{WT}$, respectively, small samples were taken after 0, 15, 30, 60, 120, 180, 360 and 540 minutes, diluted with PBS to a total volume of 1.5 ml, washed two times with 1.5 ml PBS, and loaded onto an SDS polyacrylamide gel for whole cell lysate analysis. The gel was analyzed for fluorescence using a commercially available geld documentation system (Alpha Innotech, CA) at an excitation wavelength of 365 nm and by detecting the emission with an ethidiumbromide filter setting (FIG. 3a). GFP$^{TAG \to 1}$ labeled with compound 3 was visible already after 15 min, confirming that indeed labeling of GF$^{PTAG \to 1}$ occurred.

B.4 In Vivo Labeling of Cyclooctynyl Comprising mCherry by Fluorogenic Azido Coumarin A similar experiment in B.1/B.2 was performed with *E. coli* cultures expressing either mCherry, wherein compound 1 has been incorporated at an amber-encoded site (mCherry$^{TAG \to 1}$), or wildtype mCherry (mCherry$^{WT}$). 5 ml of said cultures were harvested after overnight induction and washed two times with 12 ml PBS, resuspended in 12 ml PBS, incubated for 1 h at 4° C. in the dark, and washed another two times with 12 ml PBS. Cells were pelleted, resuspended in 3 ml PBS (OD$_{600}$~2-3) containing 50 µM azido coumarin incubated shaking at 3° C. in the dark. Cells were harvested after 3-4 h, washed two times with 1.5 ml. PBS, resuspended in 1.5 ml PBS, incubated for 1 h at 4° C. in the dark, and washed another two times with 1.5 ml PBS before cells were allowed to settle on a coverslip. Cells were then mounted on Leica SP5 microscope employing a 1.4 NA oil objective (Leica, Mannheim, Germany). Images containing 512*512 pixels were acquired at a scan speed of 400 Hz and a zoom factor of 4 yielding a final pixel size of 160.5 nm×160.5 nm. In addition to a DIC image the sample was excited using a blue diode laser operating at a wavelength of 405 nm, while simultaneously recording fluorescence signal in two channels (blue/green=420-520 nm and red=590-690 nm). Fluorescence in the blue/green channel originated from clicked coumarin while no fluorescence in the red channel originating from mCherry was visible. The same emission channels were also recorded during excitation with an DPSS laser operating at $\lambda_{ex}$=561 nm, which only excites mCherry. As a control experiment the same imaging procedure was repeated with cells expressing mCherry$^{WT}$. In this construct, the synthetase and tRNA are still active in recognizing compound 1, but mCherry$^{WT}$ contains no amber codon that allows incorporation of compound 1. Thus, in the control cells expressing mCherry$^{WT}$ only background fluorescence was visible in the blue/green channel, i.e. no compound 3 was detected in these cells. The mCherry fluorescence observed, in the red channel was stronger in the control cells than in cells expressing mCherry$^{TAG \to 1}$, since mCherry$^{WT}$ naturally expresses better than the amber suppressed mCherry$^{TAG \to 1}$.

Example C

Analysis of Fluorescence Labeled GFP$^{TAG \to 1}$ Via smFRET

C.1 Labeling of GFP$^{TAG \to 1}$ with Fluorescent Dye

To this end, GFP$^{TAG \to 1}$ was expressed and purified as described in example A. A 1 mM solution of GFP$^{TAG \to 1}$ in 4×PBS (pH 8.0) was incubated for 12 h at 37° C. with a 10 mM solution of Atto647N azide (Atto-Tec GmbH, Siegen, Germany). The mixture was incubated on Ni-NTA beads and washed with mild (2 M urea) denaturing buffer to remove any nonspecifically bound dye from the protein and then eluted in 4×PBS buffer (pH 8.0). Typical labeling efficiencies were about 50%, as determined using standard. UV/Vis spectrometry and the reported extinction coefficients for GFP, denatured GFP (if measured under denaturing conditions), and Atto647N.

C.2 Single Molecule Observation Fluorescence Resonance Energy Transfer (smFRET)

The resulting GFP$^{TAG \to 1, Atto647N}$ (Atto647N azide labeled GFP$^{TAG}$ comprising compound 1) was diluted to a concentration of 50 µM and analyzed via single molecule (sm) spectrometry of freely diffusing molecules similar to previously reported measurements schemes (Lemke et al., J. Am Chem Soc 2009, 131:13610). Briefly, the solution was mounted onto a custom built confocal microscope centered around an Olympus IX81 microscope (Hamburg, Germany) equipped with a 1.2 NA 60× water objective. The light emitting from two laser diodes (LDH 485 and 660, Picoquant, Berlin, Germany) was alternated at a master pulse frequency of 56 MHz and focused into the sample. The burst wise fluorescence light emitting from single, freely diffusing GFP$^{TAG \to 1, Atto647N}$ was spatially filtered using a 100 µm pinhole and then spectrally filtered into fluorescent donor (C) and acceptor (A) channels (using emission filters 525/50, 700/75, dichroics 500/660 and 560 from AHF, Tuebingen Germany). Single photons were detected using MPDs from Picoquant in the green and APDs (PerkinElmer, Vaudreuil Canada) in the red channel. Signals were counted using a Hydraharp (Picoquant) and subject to routine pulsed interleaved excitation analysis (Müller at al., Biophys. J. 2005, 89:3508) after binning the signal stream to a 1 ms bin width and applying a threshold of 30 counts per single molecule burst. Thus, emission bursts stemming from individual GFP$^{TAG \to 1, Atto647N}$ molecules could be analyzed based on their stochiometry (S) and for the occurrence of energy transfer (E$_{FRET}$) from D to A.

Figure 4:
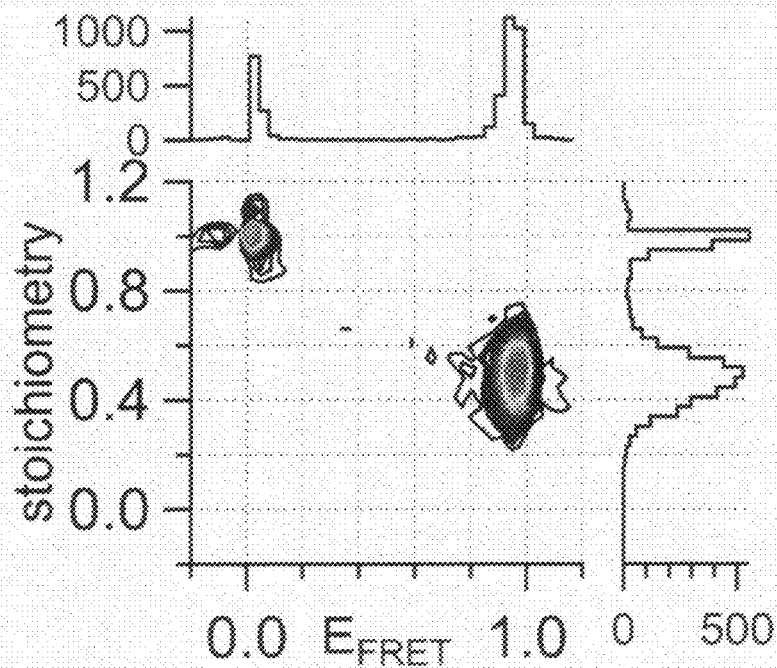
FIG. 4 shows a 2D histogram (S vs. $E_{FRET}$) of smFRET data of single freely diffusing $GFP^{TAG \to 1, Atto647N}$ molecules based on the raw data shown in FIG. 5.
Figure 5:
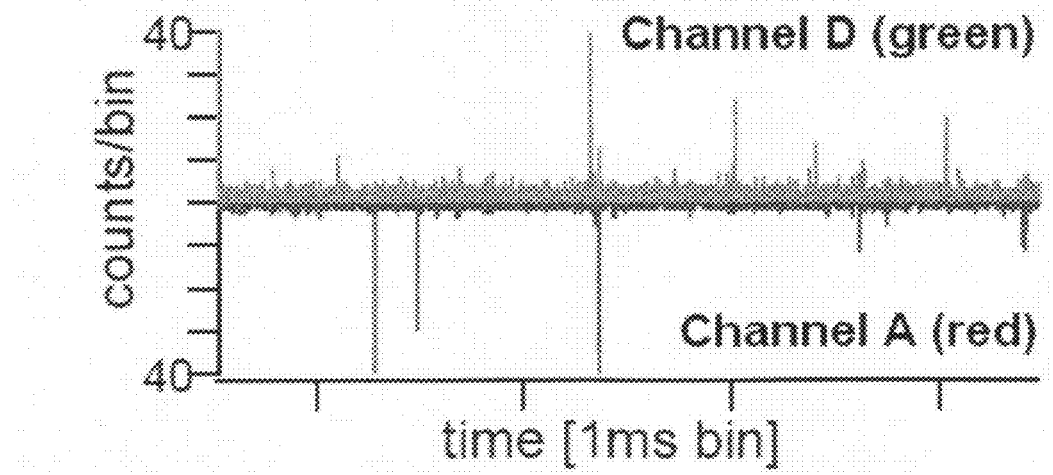
FIG. 5 shows the raw data trace (binned at 1 ms time resolution) of single freely diffusing $GFP^{TAG \to 1, Atto647N}$ corresponding to the data shown in FIG. 4. Fluorescent bursts detected in the green channel (donor, D) stem from the directly excited GFP chromophore (and little or no energy transfer to A) and bursts in the red channel (acceptor, A) originate from resonance energy transfer to the Atto647N dye.

Due to the spectral properties of the fluorescent species, the natural GFP chromophore served as a donor (D), while Atto647N served as the acceptor dye (A). At single molecule resolution using a confocal detection geometry (see above) freely diffusing. GFP$^{TAG>1, Atto647N}$ was observed (FIG. 5). Two major populations were observed (FIG. 4). One population was centered around S=1 and E$_{FRET}$=0, i.e. had only donor fluorescence. This species of molecules is almost always observed in single molecule experiments (see Lemke at al., J Am Chem Soc 2009, 131:13610) and originates from those species where A was either photo-physically inactive or not present. The second population was centered around S=0.5 and E$_{FRET}$=1, i.e. clearly identifies a species of GFP molecules labeled with Atto647N so that energy transfer occurs efficiently. The high FRET efficiency observed with this second population was well in agreement with the crystal structure of GFP (Ormö at al., Science 1996, 273:1392), indicating that the dye attached at position 39 was located within 30 Å of the GFP chromophore. No FRET signal could be observed when denaturing the protein in 6 M guanidinium hydrochloride and boiling for 5 min at 95° C. due to destruction of the GFP chromophore.

Example D

Expression of GFP and MBP with Incorporated UAAs 13, 16 and 17 in *E. coli*

D.1 GFP$^{TAG}$

GFP$^{TAG}$ with incorporated UAA 13, 16 or 17, i.e. GFP$^{TAG \to 13}$, GFP$^{TAG \to 16}$ and GFP$^{TAG \to 17}$, was prepared as described for GFP$^{TAG \to 1}$ and GFP$^{TAG \to 2}$ (see A.1) with the following exceptions. When the *E. coli* cultures reached an OD$_{600}$ between 0.2 and 0.3, instead of compounds 1 or 2 compound 13, 16 or 17, respectively, (stock solution 80 mM in 0.1 M NaOH) or an equal amount of 0.1 M NaOH (for negative control experiments) were added to a final concentration of 1 mM. GFP$^{TAG \to 13}$ was purified using Macro-Prep HIC support instead of Ni beads following the manufacturer's protocol (BIO-RAD, Munich, Germany).

Figure 6:
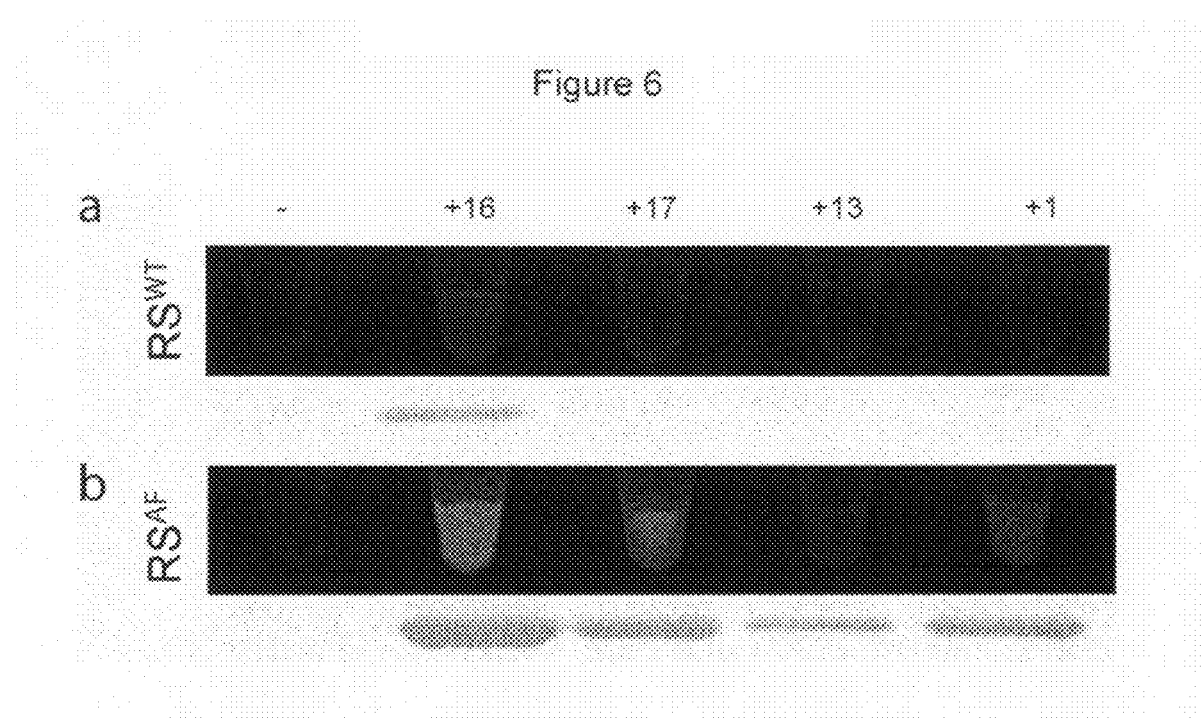
FIG. 6 shows fluorescent images of *E. coli* suspensions in microcentrifuge tubes expressing $GFP^{TAG}$ in the absence ("−") and presence ("+") of UAAs 1, 13, 16 or 17, respectively, with the corresponding Coomassie stained SDS polyacrylamide gel after purification of the $GFP^{TAG}$ obtained in *E. coli* cotransfected with plasmids encoding $RS^{WT}$ (a) or $RS^{AF}$ (b).

The *E. coli* cells were examined for GFP fluorescence, and the purified proteins were separated by SDS-PAGE and Coomassie stained (FIG. 6). The results show efficient incorporation of compounds 1, 13, 16 and 17 by RS$^{AF}$. Incorporation by RS$^{WT}$ was lower with highest GFP$^{TAG}$ expression, in the presence of compound 16.

D.2 MBP$^{TAG}$

A maltose binding protein (MBP) with an amber stop codon at the permissive site 38 and a C-terminal His tag (MBP$^{TAG}$) was used for expression by *E. coli* in the presence of UAAs analogously to GPF$^{TAG}$. Protein expression, lysis and purification were performed as described in A.1 and D.1.

MBP$^{TAG \to 1}$, MBP$^{TAG \to 13}$, MBP$^{TAG \to 16}$, and MBP$^{TAG \to 17}$ purified from said *E. coli* were analyzed using a Quadrupole Time of Flight electrospray tandem mass spectrometer (Q-ToF, Waters). The results summarized in Table 3 confirm incorporation of the respective UAA into the MBP$^{TAG}$.

TABLE 3

Mass spectrometry of MBP$^{TAG \to 1}$, MBP$^{TAG \to 13}$, MBP$^{TAG \to 16}$, and MBP$^{TAG \to 17}$ purified from *E. coli*. Results are given as differences ($\Delta$) to MBP$^{TAG \to AcF}$. AcF (p-acetylphenylalanine) is an UAA with a phenylalanine backbone.

| UAA | MW [Da] (calculated) | $\Delta$MW [Da] to AcF (calculated) | protein | $\Delta$MW [Da] (observed) to MBP$^{TAG \to AcF}$ (calculated) |
|---|---|---|---|---|
| AcF | 207 | 0 | MBP$^{TAG \to AcF}$ | 0 |
| compound 1 | 296 | 89 | MBP$^{TAG \to 17}$ | 85 |
| compound 13 | 298 | 91 | MBP$^{TAG \to 16}$ | 91 |
| compound 16 | 282 | 75 | MBP$^{TAG \to 1}$ | 78 |
| compound 17 | 296 | 89 | MBP$^{TAG \to 13}$ | 88 |

Example E

In Vivo Fluorescence Labeling of *E. Coli* Expressed GFP and MBP with Incorporated UAAs E.1 Visualization of In Vivo Labeled GFP$^{TAG}$ Proteins Separated by SDS-PAGE GFP$^{TAG \to 1}$, GFP$^{TAG \to 13}$, GFP$^{TAG \to 16}$ and GFP$^{TAG \to 17}$ were expressed in *E. coli* as described in examples A and D and labeled with either TAMRA-azide (Az), or TAMRA-tetrazine (Tet) (both 50 µM for 12 h at 37° C.). GFP$^{TAG}$ expressed with the UAA propargyllysine was used as a negative control as aliphatic alkynes can only perform copper(I)-catalyzed azide-alkyne cycloaddition and not strain promoted azide-alkyne reactions. The *E. coli* expressed proteins were separated by SDS-PAGE, and visualized by Coomassie staining (FIG. 7b) and fluorescence scan (FIG. 7a). Fluorescence observed at the height of the GFP band verified successful labeling. Each of GFP$^{TAG \to 1}$, GFP$^{TAG \to 13}$, GFP$^{TAG \to 16}$ and GFP$^{TAG \to 17}$ was successfully labeled with TAMRA-tetrazine. Only the protein comprising a cyclooctynyl residue, i.e. GFP$^{TAG \to 1}$, was labeled with TAMRA-azide.

E.2 Visualization of In Vivo Labeled MBP$^{TAG}$ by Fluorescence Microscopy

*E. coli* expressing MBP$^{TAG}$ in the presence of compound 1 or compound 17 were cultured separately and then washed four times with PBS. The two *E. coli* cultures were mixed 1:1 (OD$_{600}$~2) and incubated with 50 µM TAMRA-azide for 4 h at 37° C. Then the *E. coli* were washed once with PBS before incubation was continued with 10 µM coumarin-tetrazine for 4 h at 37° C. As controls *E. coli* expressing MBP$^{TAG \to 1}$ and *E. coli* expressing MBP$^{TAG \to 17}$ were labeled separately with TAMRA-azide or coumarin-tetrazine, respectively. After labeling, all cultures were washed five times with PBS containing 5% DMSO to get rid of excess dye. The resulting images showed green (MBP$^{TAG \to 17}$ labeled with coumarin-tetrazine) and red (MBP$^{TAG \to 1}$ labeled with TAMRA-azide) fluorescent cells. MBP$^{TAG \to 17}$ treated with TAMRA-azide did not show any fluorescence, while MBP$^{TAG \to 1}$ labeled with coumarin-tetrazine showed green fluorescent cells.

TABLE 4

In vivo imaging of *E. coli* expressing MBP$^{TAG \to 1}$ and MBP$^{TAG \to 17}$ labeled with coumarin-tetrazine and TAMRA-azide. Fluorescence of cells indicated: coumarin = green and TAMRA = red.

| *E. coli* expressing | coumarin-tetrazine | TAMRA-azide | coumarin/TAMRA overlay |
|---|---|---|---|
| MBP$^{TAG \to 1}$ and MBP$^{TAG \to 17}$ (mixed) | green | red | green + red |
| MBP$^{TAG \to 1}$ | green | no fluorescence | green |
| MBP$^{TAG \to 17}$ | no fluorescence (not stained) | only background fluorescence | only background fluorescence |

E.3 Quantitative Analysis of In Vivo TAMRA Labeling by FRET

GFP$^{TAG}$ with incorporated compound 1, 13, 16 or 17 was expressed in *E. coli* as described in examples A and D. *E. coli* lysate was adjusted to a final GFP concentration of about 500 nM based on absorbance spectra. 5 µM dye (TAMRA-tetrazine or TAMRA-azide) were added and fluorescence spectra (excitation at 450 nm, emission 470-650 nm) were recorded. Successful labeling of GFP$^{TAG}$ was monitored, by FRET from the GFP chromophore to TAMRA when attached to the protein. In the individual spectra this was visible by a decrease of GFP-fluorescence (around 505 nm) and a simultaneous increase of TAMRA-fluorescence (abound 575 nm) over time (dark- to light-colored graph) as shown exemplarily for GFP$^{TAG \to 13}$ in FIG. 8).

For evaluation of the corresponding time traces, all data was corrected for direct excitation (i.e. excitation of TAMRA by the excitation light) and leakage (emission of GFP into the acceptor signal) using the first time point (where the reaction has not yet proceeded substantially). For GFP$^{TAG \to 13}$ the reaction was so fast that leakage, and direct excitation values from separate control experiments were used. To observe slower reactions and extract rate constants purified GFP$^{TAG}$ with incorporated UAA was adjusted to a final concentration of about 1 µM based on absorbance spectra. 5 µM TAMRA-tetrazine were added and fluorescence spectra (excitation at 450 nm, emission 470-650 nm) were recorded for several hours. In case of compound 1 reacting with TAMRA-azide, the concentration of azide was increased to 50 µM to achieve labeling in a reasonable time scale. Resulting reaction kinetics were fit with a simple monoexponential model according to $GFP^{UAA \rightarrow TAMRA}(t) = A_0(1-\exp(-kBt))$, where $A_0$ corresponds to the amplitude of the fit and is proportional to the initial GFP-concentration, and B corresponds to the concentration of dye within the reaction. The rate constant, k, of the reaction was obtained from the fit under the assumption of constant B during the reaction (which is valid due to the large dye excess). Approximate rate constants measured at 37° C. are summarized Table 5.

TABLE 5

In vitro reaction kinetics of
$GFP^{TAG}$ with incorporated 1, 13, 16 or 17.

| | labeled with | |
|---|---|---|
| | TAMRA-tetrazine [1/s] | TAMRA-azide [1/s] |
| $GFP^{TAG \rightarrow 1}$ | ~65 | ~1 |
| $GFP^{TAG \rightarrow 13}$ | ~40,000 | no reaction |
| $GFP^{TAG \rightarrow 16}$ | ~6 | no reaction |
| $GFP^{TAG \rightarrow 17}$ | ~8 | no reaction |

Example F

Expression of GFP and MBP with Incorporated UAAs 1, 13, 16 and 17 in Mammalian Cells F.1 Plasmids and DNA Constructs A single expression plasmid for expression of both $tRNA^{pyl}$ and the pyrrolysine synthetase pylRS was generated by replacing the tRNA and synthetase of mammalian UAA expression plasmid pSWAN (Liu et al., Nat Methods 2007, 4: 239) with a synthetic gene derived from the plasmid pEVOL $tRNA^{pyl}$/pylRS$^{WT}$ or pEVOL $tRNA^{pyl}$/pylRS$^{AF}$. This resulted in the generation of plasmids pCMV $tRNA^{pyl}$/pylRS$^{WT}$ and pCMV $tRNA^{pyl}$/pylRS$^{AF}$ that were used for co-transfection of mammalian cells.

For mammalian amber suppression studies, a NLS-mCherry-$^{TAG}$GFP fusion protein was generated. Due to the nuclear localization sequence (NLS) the expressed protein was targeted to the nucleus. Accordingly, mCherry expression was visible by orange fluorescence in the nucleus signifying the successful transfection of the plasmid. Green fluorescence indicated successful GFP expression due to successful co-transfection of the appropriate $tRNA^{pyl}$/pylRS plasmid and suppression of the amber codon in the fused $^{TAG}$GFP.

F.2 Automated Microscope Procedure for Determining UAA Dependent Amber Suppression UAA concentration dependent GFP expression in the presence of UAA 1, 13, 16 or 17 and RS$^{WT}$ or RS$^{AF}$ was analyzed using the following automated microscope procedure.

HeLa Kyoto cells were grown in DMEM low glucose medium (1 g/l) (Sigma, Munich, Germany) with 10% FBS (Sigma) and 1% L-glutamine. 10–20×10$^3$ cells per well were seeded in a glass bottom 24-well chamber and cultured overnight. On the next-day, the growth medium was exchanged for fresh one supplied with increasing concentrations of UAA (0, 1, 10, 100, 250, 1000 μM), and the cells were co-transfected (1:1 ratio) with plasmids-carrying NLS-mCherry-$^{TAG}$-GFP and the respective $tRNA^{pyl}$/pylRS pair (RS$^{WT}$ or RS$^{AF}$) using jetPRIME transfection reagent following the manufacturer protocol (Polyplus-transfection. SA, Illkirch, France). 24 h after transfection, cells were stained with Hoechst 33342 (1 μg/ml, 10 min), fixed with 2% paraformaldehyde (15 min, RT) and kept in PBS for imaging. For every UAA concentration, the experiment was repeated twice and in two independently prepared 24 well chambers.

Microscopy imaging was performed using automated widefield Olympus ScanR microscope (objective UplanApo 20×, 0.70 NA, Hamamatsu Orca R2 CCD camera) in three channels (Hoechst, GFP, mCherry). For every well at least 25 images (1344×1024 pixels; 433×330 μm, 12-bit) were acquired (exposure times: 30 ms Hoechst, 100 ms mCherry, 100 ms for GFP). Hoechst staining allowed use of the automated focus option of the system. Images were analyzed using the ImageJ macro (http://fiji.sc/wiki/index.php) allowing quantification of GFP fluorescence intensity in the cells showing mCherry fluorescence signal. Hoechst staining was used to threshold and select nuclei. For every detected nucleus, intensities, in the mCherry and GFP channels were quantified. Background intensities in GFP and mCherry channel were measured using one well of each chamber containing cells that were not transfected but stained with Hoechst. Those background values set the threshold to discriminate cells expressing mCherry from the background. For every well the average intensity of GFP ($I_{GFP}$) in cells positive for GFP and mCherry signals was determined as a measure of successful UAA incorporation. GFP intensities were normalized separately for every UAA based on the maximal observed signal (either for RS$^{WT}$ or RS$^{AF}$).

Normalized $I_{GFP}$ data are summarized in Table 6. NLS-mCherry-$^{TAG}$GFP fusion protein fusion protein expression was detected for all UAAs in a clearly UAA concentration dependent manner. Fusion protein expression typically showed an optimum around 250 μM. UAA.

TABLE 6

GFP fluorescence intensities in nuclei of co-transfected HeLa cells. Indicated are average intensities of GFP ($I_{GFP}$) and standard deviations (SD).

| | compound 1 | | | | compound 13 | | | |
|---|---|---|---|---|---|---|---|---|
| concentration | RS$^{WT}$ | | RS$^{AF}$ | | RS$^{WT}$ | | RS$^{AF}$ | |
| of UAA [μM] | $I_{GFP}$ | SD | $I_{GFP}$ | SD | $I_{GFP}$ | SD | $I_{GFP}$ | SD |
| 0 | 0.0 | 0.0 | 7.0 | 0.4 | 7.9 | 0.4 | 6.5 | 0.6 |
| 1 | 3.3 | 0.4 | 23.7 | 2.0 | 6.3 | 0.3 | 11.1 | 0.6 |
| 10 | 5.9 | 0.7 | 131.7 | 9.0 | 6.9 | 0.5 | 11.0 | 0.6 |
| 100 | 27.6 | 3.7 | 106.1 | 12.0 | 15.9 | 0.8 | 28.8 | 1.9 |
| 250 | 59.6 | 4.5 | 203.6 | 8.8 | 22.3 | 1.6 | 36.5 | 3.7 |
| 1000 | 57.5 | 8.0 | 118.4 | 12.0 | 33.2 | 1.9 | 20.6 | 2.2 |

| | compound 16 | | | | compound 17 | | | |
|---|---|---|---|---|---|---|---|---|
| concentration | RS$^{WT}$ | | RS$^{AF}$ | | RS$^{WT}$ | | RS$^{AF}$ | |
| of UAA [μM] | $I_{GFP}$ | SD | $I_{GFP}$ | SD | $I_{GFP}$ | SD | $I_{GFP}$ | SD |
| 0 | 1.8 | 0.4 | 11.6 | 1.3 | 5.7 | 0.5 | 3.8 | 0.2 |
| 1 | 1.5 | 0.4 | 5.7 | 0.7 | 4.2 | 0.3 | 10.9 | 1.2 |
| 10 | 6.9 | 0.8 | 46.1 | 11.3 | 2.6 | 0.2 | 57.5 | 4.6 |
| 100 | 9.4 | 2.2 | 114.8 | 9.0 | 4.3 | 0.5 | 76.6 | 10.0 |
| 250 | 171.6 | 10.5 | 100.4 | 22.4 | 5.7 | 0.5 | 163.5 | 8.8 |
| 1000 | 178.3 | 11.8 | 96.9 | 68.7 | 12.8 | 1.1 | 108.9 | 9.8 |

ABBREVIATIONS

AcF=p-acetylphenylalanine
AcOH=acetic acid
Boc-L-Lys-OH=N-α-tert-butyloxycarbonyl-L-lysine
cHex=cyclohexane
DBU=1,8-diazabicyclo[5.4.0]undec-7-ene
DCM=dichloromethane DMF=dimethylformamide
DMSO=dimethylsulfoxide
EtOH=ethanol
EtOAc=ethyl acetate
FC=flash chromatography
FRET=fluorescence resonance energy transfer, also called Förster resonance energy transfer
MeOH=Methanol
GFP=green fluorescent protein
$GFP^{WT}$=wildtype GFP
$GFP^{TAG}$=GFP encoded by a sequence comprising amber stop codon TAG at permissive site 39
$GFP^{\rightarrow 1}$=$GFP^{TAG}$ wherein compound 1 has been incorporated at amber-encoded site
$I_{GFP}$=average intensity of GFP
MBP=maltose binding protein
MBPTAG=MBP encoded by a sequence comprising amber stop codon TAG at permissive site 38 and a C-terminal His tag
$MBP^{TAG\rightarrow 1}$=$MBP^{TAG}$ wherein compound 1 has been incorporated at amber-encoded site
$mCherry^{Wt}$=wildtype mCherry
$mCherry^{TAG\rightarrow 1}$=mCherry wherein compound 1 has been incorporated at amber-encoded site
NLS=nuclear localisation sequence
$OD_{600}$=optical density at 600 nm
PBS=phosphate buffered saline
PMSF=Phenylmethylsulfonylfluoride
RT=room temperature
SD=standard deviation
SDS-PAGE=sodium sodecyl sulfate polyacrylamide gel electrophoresis
smFRET=single molecule observation of FRET
TAMRA=tetramethylrhodamine
TB=Terrific Broth
TEA=triethylamine
THF=tetrahydrofurane
TLC=thin layer chromatography
UAA=unnatural amino acid

---

The invention claimed is:
1. A compound of formula I

wherein:
X¹ has formula

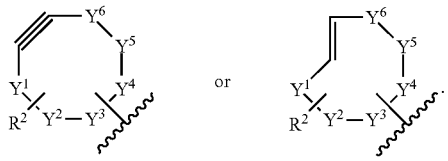

wherein:
Y¹, Y², Y³, Y⁵, Y⁶ independently are —CH₂—, —NH—, —S— or —O— provided that at least 4 of Y¹, Y², Y³, Y⁴, Y⁵, Y⁶ are —CH₂—;
R² is hydrogen, halogen, C₁-C₄-alkyl, CF₃, CN, C₁-C₄-alkoxy, —O—CF₃, C₂-C₅-alkanoyloxy, C₁-C₄-alkylaminocarbonyloxy or C₁-C₄-alkylthio;
X² is —CH₂—, —O—, —S—, —NH—, —C(O)—, —OC(O)—, —C(O)O—, —NH—C(O)— or —C(O)—NH—, or
X² is >CH— or >N— wherein the carbon or the nitrogen atom together with two adjacent ring atoms of X¹ forms a 3-membered ring, or
X² is —CH₂—CH<, —NH—CH< or —CH₂—N< wherein the two carbon atoms or the carbon and the nitrogen atom together with two adjacent ring atoms of X¹ form a 4-membered ring, or
X² is —CH₂—CH₂—CH<, —NH—CH₂—CH<, —CH₂—NH—CH<, —CH₂—CH₂—N<,

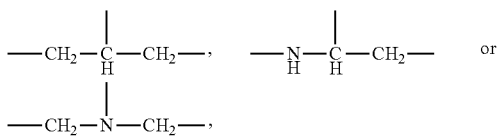

wherein the three carbon atoms or the two carbon atoms and the nitrogen atom together with two adjacent ring atoms of X¹ form a 5-membered ring;
X³ is C₁-C₆-alkylene, —(CH₂—CH₂—O)$_m$—, —(CH₂—O)$_p$— or a single bond;
X⁴ is —NH—, —C(O)—NH—, —NH—C(O)—, —NH—CH(NH₂)—, —CH(NH₂)—NH—, —NH—C(NH)—NH—, —C(O)—NH—CH(NH₂)—, —C(O)—NH—C(NH)—NH—, NH—CH(NH₂)—C(O)— or —NH—C(NH)—NH—C(O)—;
X⁵ is hydrogen, C₁-C₆-alkyl, C₁-C₆-alkoxy-C₁-C₂-alkyl, C₂-C₇-alkanoyloxy-C₁-C₂-alkyl or C₂-C₇-alkanoylsulfanyl-C₁-C₂-alkyl;
R¹ is —OH or —NH₂;
n is an integer from 1 to 4;
m is an integer from 1 to 6; and
p is an integer from 1 to 6,
or an acid or base addition salt thereof.

2. The compound or salt of claim 1, wherein R² is hydrogen or halogen.
3. The compound or salt of claim 2, wherein R² is fluorine.
4. The compound or salt of claim 3, wherein R² is two fluorine bound to one carbon ring atom.
5. The compound or salt of claim 1, wherein X¹ has the formula

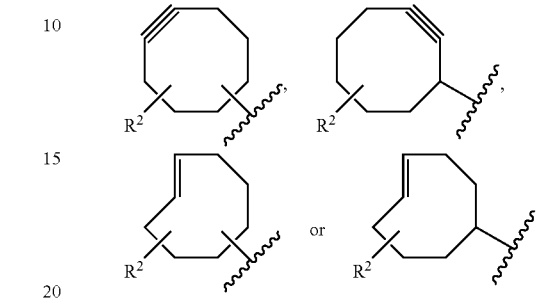

wherein R² is as defined in claim 1.
6. The compound or salt of claim 1, wherein one of Y¹, Y², Y³, Y⁴, Y⁵, Y⁶ is —NH— while the remaining five of Y¹, Y², Y³, Y⁴, Y⁵, Y⁶ are —CH₂—, and R² is as defined in claim 1.
7. The compound or salt of claim 1, wherein X¹ has a formula selected from

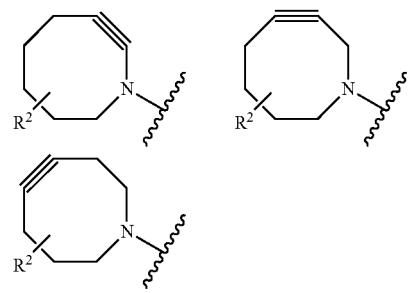

and R² is as defined in claim 1.
8. The compound or salt of claim 1, wherein X¹ is unsubstituted cyclooctynyl or cyclooctynyl substituted with one or two halogen atoms.
9. The compound or salt of claim 8, wherein the halogen atoms are fluorine atoms.
10. The compound or salt of claim 1, wherein X¹ is unsubstituted trans-cyclooctenyl.
11. The compound or salt of claim 1, wherein X² is —O—.
12. The compound or salt of claim 1, wherein X³ is —CH₂—CH₂—O— or a single bond.
13. The compound or salt of claim 1, wherein the structural element —X²-X³— comprises from 1 to 6 atoms in the main chain.
14. The compound or salt of claim 1, wherein X⁴ is —NH—, —C(O)—NH—, —NH—CH(NH₂)—, —NH—C(NH)—NH—, —C(O)—NH—CH(NH₂)— or —C(O)—NH—C(NH)—NH—.
15. The compound or salt of claim 1, wherein n is 3 or 4.
16. The compound or salt of claim 1, wherein the structural element —X²-X³-X⁴—(CH₂)$_n$— comprises from 5 to 12 atoms in the main chain, such as 6, 7, 8, 9, 10 or 11 atoms in the main chain.
17. The compound or salt of claim 1, wherein X⁵ is hydrogen, C₁-C₆-alkoxymethyl, C₁-C₆-alkoxyeth-1-yl, C₂-C₇-alkanoyloxymethyl or C₂-C₇-alkanoylsulfanylethyl.

18. The compound or salt of claim 1, having S-configuration with regard to the asymmetric carbon atom carrying $R^1$.

19. The compound or salt of claim 1, wherein —$(CH_2)_n$—$CHR^1$—$C(O)O$—$X^5$ has formula

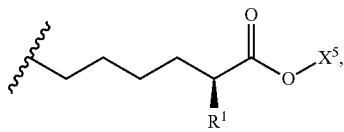

wherein $R^1$ and $X^5$ are as defined in claim 1.

20. The compound or salt of claim 1 that is a compound of formula Ia, Ib, Ic or Id

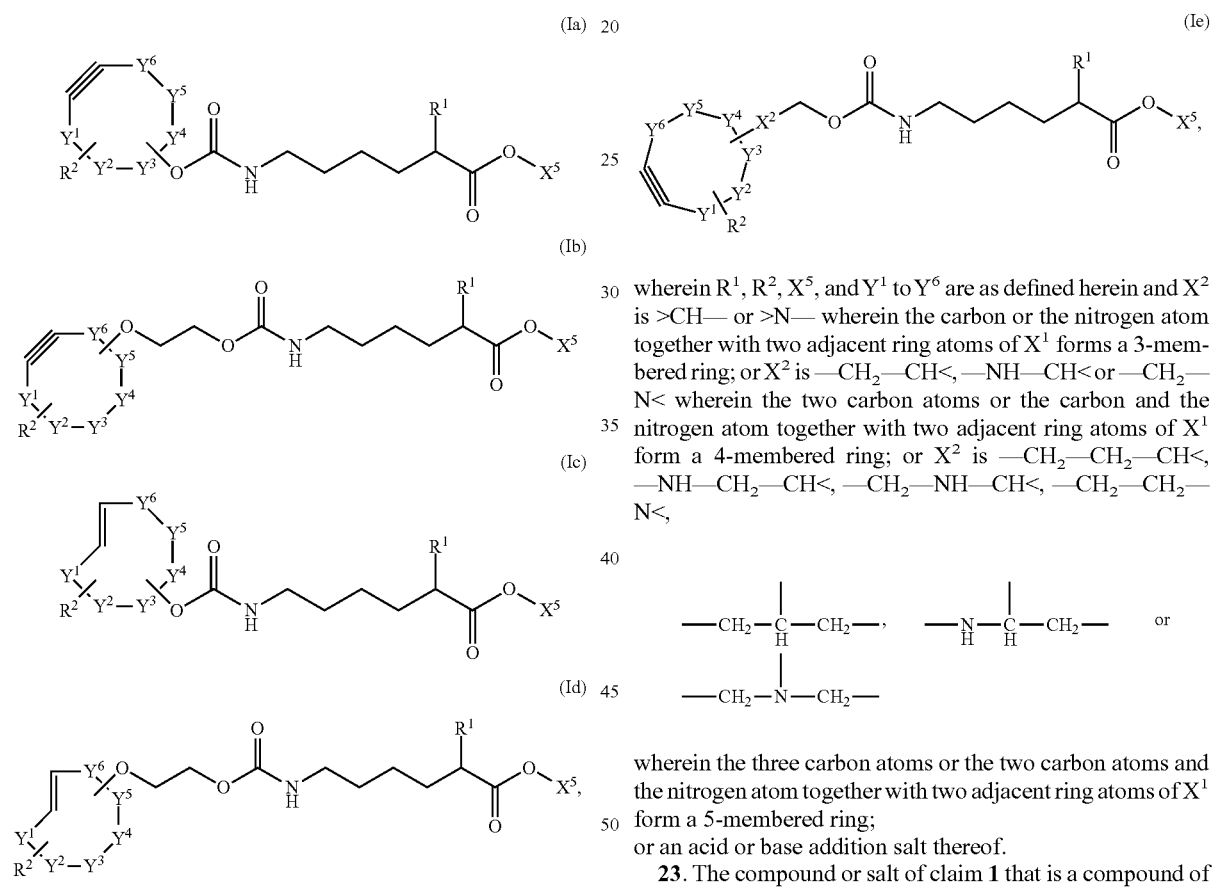

wherein $R^1$, $R^2$, $X^5$, and $Y^1$ to $Y^6$ are as defined in claim 1, or an acid or base addition salt thereof.

21. The compound or salt of claim 1 that is a compound of formula

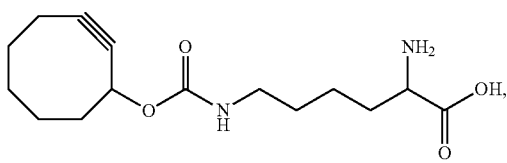

or an acid or base addition salt thereof.

22. The compound or salt of claim 1 that is a compound of formula Ie

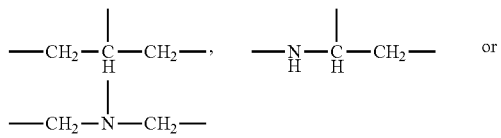

wherein $R^1$, $R^2$, $X^5$, and $Y^1$ to $Y^6$ are as defined herein and $X^2$ is >CH— or >N— wherein the carbon or the nitrogen atom together with two adjacent ring atoms of $X^1$ forms a 3-membered ring; or $X^2$ is —$CH_2$—CH<, —NH—CH< or —$CH_2$—N< wherein the two carbon atoms or the carbon and the nitrogen atom together with two adjacent ring atoms of $X^1$ form a 4-membered ring; or $X^2$ is —$CH_2$—$CH_2$—CH<, —NH—$CH_2$—CH<, —$CH_2$—NH—CH<, —$CH_2$—$CH_2$—N<, $$-CH_2-\underset{H}{\overset{|}{C}}-CH_2-, \quad -N-\underset{H}{\overset{|}{\underset{H}{C}}}-CH_2- \quad \text{or}$$

$$-CH_2-\underset{|}{N}-CH_2-$$

wherein the three carbon atoms or the two carbon atoms and the nitrogen atom together with two adjacent ring atoms of $X^1$ form a 5-membered ring;
or an acid or base addition salt thereof.

23. The compound or salt of claim 1 that is a compound of formula

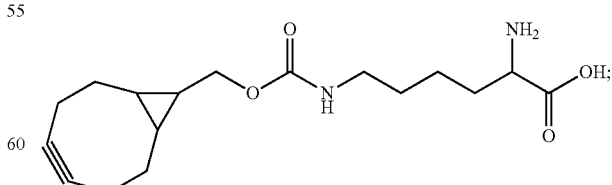

or an acid or base addition salt thereof.

24. A process for preparing a target polypeptide having one or more than one cyclooctynyl or trans-cyclooctenyl analog group, the process comprising:

a) providing a translation system comprising:
   (i) an aminoacyl tRNA synthetase, or a polynucleotide encoding it;
   (ii) a compound or salt of claim 1;
   (iii) a tRNA having an anticodon to a selector codon, or a polynucleotide encoding said tRNA; and
   (iv) a polynucleotide encoding the target polypeptide and comprising one or more than one selector codon(s),
   wherein the aminoacyl tRNA synthetase (i) is capable of specifically acylating the tRNA (iii) with the compound or salt (ii);
b) allowing translation of the polynucleotide (iv) thereby incorporating the compound (ii) into the target polypeptide at the position(s) encoded by the selector codon(s).

25. The process of claim 24, wherein said translation system is a cell expressing said aminoacyl tRNA synthetase.

26. The process of claim 24, wherein said aminoacyl tRNA synthetase is a pyrrolysyl tRNA synthetase.

27. The process of claim 26, wherein said pyrrolysyl tRNA synthetase comprises the amino acid sequence set forth in SEQ ID NO:1 or 2.

28. A polypeptide comprising one or more than one residue of formula II

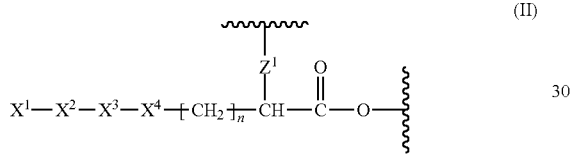

(II)

wherein:
$X^1$ has the formula

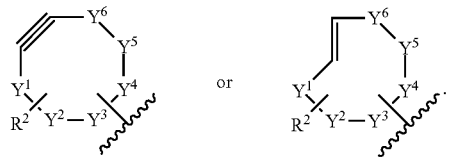

or wherein:
$Y^1, Y^2, Y^3, Y^4, Y^5, Y^6$ independently are —$CH_2$—, —NH—, —S— or —O— provided that at least 4 of $Y^1, Y^2, Y^3, Y^4, Y^5, Y^6$ are —$CH_2$— or;

$R^2$ is hydrogen, halogen, $C_1$-$C_4$-alkyl, $CF_3$, CN, $C_1$-$C_4$-alkoxy, —O—$CF_3$, $C_2$-$C_5$-alkanoyloxy, $C_1$-$C_4$-alkylaminocarbonyloxy or $C_1$-$C_4$-alkylthio;

$X^2$ is —$CH_2$—, —O—, —S—, —NH—, —C(O)—, —OC(O)—, —C(O)O—, —NH—C(O)— or —C(O)—NH— or $X^2$ is >CH— or >N— wherein the carbon or the nitrogen atom together with two adjacent ring atoms of $X^1$ forms a 3-membered ring, or $X^2$ is —$CH_2$—CH<, —NH—CH< or —$CH_2$—N< wherein the two carbon atoms or the carbon and the nitrogen atom together with two adjacent ring atoms of $X^1$ form a 4-membered ring, or $X^2$ is —$CH_2$—$CH_2$—CH<, —NH—$CH_2$—CH<, —$CH_2$—NH—CH<, —$CH_2$—$CH_2$—N<,

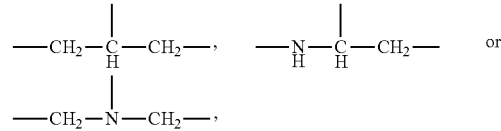

wherein the three carbon atoms or the two carbon atoms and the nitrogen atom together with two adjacent ring atoms of $X^1$ form a 5-membered ring;

$X^3$ is $C_1$-$C_6$-alkylene, —($CH_2$—$CH_2$—O)$_m$—, —($CH_2$—O)$_p$— or a single bond;

$X^4$ is —NH—, —C(O)—NH—, —NH—C(O)—, —NH—CH($NH_2$)—, —CH($NH_2$)—NH—, —NH—C(NH)—NH—, —C(O)—NH—CH($NH_2$)—, —C(O)—NH—C(NH)—NH—, NH—CH($NH_2$)—C(O)— or —NH—C(NH)—NH—C(O)—;

$Z^1$ is —O— or —NH—;

n is an integer from 1 to 4;

m is an integer from 1 to 6; and p is an integer from 1 to 6.

29. A kit for preparing a polypeptide having one or more than one cyclooctynyl or trans-cyclooctenyl analog group, comprising the compound or salt of claim 1.

* * * * *